(12) United States Patent
Xia

(10) Patent No.: US 11,998,713 B2
(45) Date of Patent: *Jun. 4, 2024

(54) INTRODUCTION NEEDLE AND TATTOO DEVICE

(71) Applicant: Tingting Xia, Jiangsu (CN)

(72) Inventor: Tingting Xia, Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/243,091

(22) Filed: Sep. 6, 2023

(65) Prior Publication Data

US 2023/0414914 A1 Dec. 28, 2023

Related U.S. Application Data

(63) Continuation of application No. PCT/CN2022/071556, filed on Jan. 12, 2022.

(30) Foreign Application Priority Data

Apr. 14, 2021 (CN) .......................... 202110402463.0

(51) Int. Cl.
*A61M 37/00* (2006.01)
(52) U.S. Cl.
CPC .............................. *A61M 37/0084* (2013.01)
(58) Field of Classification Search
CPC .......... A61M 37/0076; A61M 37/0084; A61M 2202/0007; A61M 2205/106; A61M 2205/8281; A61M 2210/04; A61M 5/46
See application file for complete search history.

(56) References Cited

U.S. PATENT DOCUMENTS

| D888,240 S | * | 6/2020 | Parcon | .............. A61M 37/0076 |
| | | | | D24/146 |
| 2011/0009860 A1 | * | 1/2011 | Chornenky | ............ A61B 18/14 |
| | | | | 606/41 |
| 2019/0217072 A1 | * | 7/2019 | Xiao | ................. A61M 37/0084 |

FOREIGN PATENT DOCUMENTS

| CN | 202777447 U | 3/2013 |
| CN | 207520450 U | 6/2018 |
| CN | 209286492 U | 8/2019 |
| CN | 211561565 U | 9/2020 |

OTHER PUBLICATIONS

International Search Report of PCT Patent Application No. PCT/CN2022/071556 dated Mar. 30, 2022.

* cited by examiner

*Primary Examiner* — Robert A Lynch

(57) ABSTRACT

An introduction needle includes a needle piercing portion. The needle piercing portion comprises a piercing projection, the piercing projection includes a substrate and a needle tooth, the needle tooth is fixedly arranged on a side surface of a side of the substrate, a central axis of the needle tooth is perpendicular to the side surface of the substrate.

19 Claims, 41 Drawing Sheets

INTRODUCTION NEEDLE AND TATTOO DEVICE

CROSS REFERENCE TO RELATED APPLICATIONS

The present application is a continuation of PCT patent application No. PCT/CN2022/071556, filed on Jan. 12, 2022, which claims the benefit of Chinese Patent Application No. 202110402463.0 filed on Apr. 14, 2021. All the above are hereby incorporated by reference in their entirety.

TECHNICAL FIELD

The present disclosure relates to the field of tattoo tools, and in particular to an introduction needle and a tattoo device.

BACKGROUND

Tattoo is a method of embellish a face by introducing a colour pigment into a certain depth of the skin, and the colour pigment may be retained for months to years. A working principle of tattoo is disrupting the skin and applying color to the skin. An essential component of a tattoo tool in the art is a metal needle filament having one sharpened end. As demands of users are changed, semi-permanent tattoo has emerged in the art. For the semi-permanent tattoo, based on the principle of disrupting the skin and applying color to the skin, the pigment is retained at a shallower layer of the skin, i.e., at a layer between the epidermis and the dermis, or at a layer of the dermis near the epidermis. For a tattoo obtained in this way, the colour may be retained for 1-2 years and may be metabolized naturally.

Tattoo is actually coloring the skin by minimal invasion. The pigment is planted in the skin tissue to form a stable colour block. Since the epidermis is quite thin and is semi-translucent, the color of the pigment can be observed through the epidermis layer to cover up defects, to express the beauty but avoid shortcomings, and to modify and embellish the skin. Any pigment that is introduced into the skin is in a form of a small particle, and a diameter of the small particle is less than one micrometer. The small particle may be quickly surrounded by collagen but cannot be phagocytosed by phagocytes, and therefore, a mark is formed on the skin.

While producing a tattoo, a tattooist needs to use a tattoo tool to leave a mark on the skin. In order to produce the tattoo, which may be retained in the skin for 1 to 2 year and metabolized naturally afterwards, the tattooist needs to accurately control, while producing the tattoo, a depth that the needle reaches in the skin, and that is, a length that a needle projects out of the tattoo tool must be accurately adjusted. However, in the art, the tattoo tool cannot accurately control a length that the metal needle filament at a front end of the tattoo tool projects out of the tattoo tool and the depth that the needle reaches in the skin. The tattooist has to adjust, by naked eyes and based on experience, the length that the metal needle filament at the front end of the tattoo tool projects out of the tattoo tool. While the tattoo tool is started up for adjustment, the tattooist has to adjust, by naked eyes, the length that the metal needle filament projects out of the tattoo tool while the needle filament is extending and retracting at a high speed. The adjustment, performed based on experience, may have a large error rate, it may be difficult for learners to learn the method, and the tattoo method may not be easily industrialized.

Therefore, it is urgent to propose a technical solution to solve the problems in the art.

SUMMARY OF THE DISCLOSURE

In order to solve the problems in the art, the present disclosure provides an introduction needle and a tattoo device, the technical solutions are as follows.

An introduction needle includes a needle piercing portion. The needle piercing portion comprises a piercing projection, the piercing projection includes a substrate and a needle tooth, the needle tooth is fixedly arranged on a side surface of the substrate, a central axis of the needle tooth is perpendicular to the side surface of the substrate.

The present disclosure further provides a tattoo device including the above-described introduction needle.

BRIEF DESCRIPTION OF THE DRAWINGS

In order to more clearly illustrate the technical solutions in the embodiments of the present disclosure or in the art, the accompanying drawings for the description of the embodiments or the art will be briefly introduced below. Obviously, the accompanying drawings in the following description are only some of the embodiments of the present disclosure. Any ordinary skilled person in the art may obtain other drawings based on the accompanying drawings without creative work.

Figure 1A:
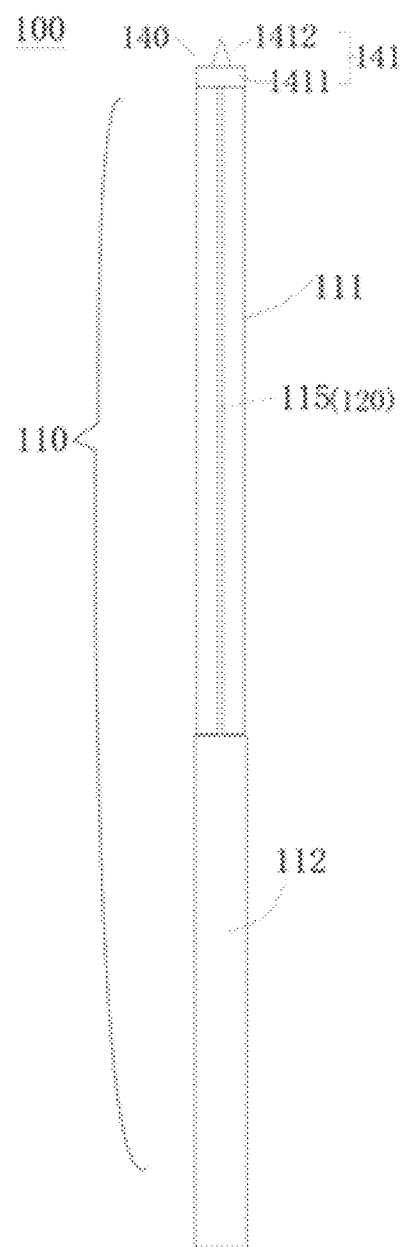
FIG. 1(a) is a structural schematic view of an introduction needle according to an embodiment of the present disclosure.

Reference numerals are as follows:
100—Introduction needle;
110—liquid guiding member; 111—liquid guiding post; 1111—first end face; 1112—second end face; 112—connecting rod; 113—flat-end needle filament; 114—small post; 115—channel;
120—capillary liquid storage unit;
130—liquid storage structure; 131—fiber filament;
140—needle piercing portion; 141—piercing projection; 1411—substrate; 1412—needle tooth;
150—case; 151—fastening end; 152—intermediate connecting tube; 153—needle outlet end; 1531—needle outlet port;
160—limiting structure; 161—limiting hole; 162—limiting tube; 163—limiting bracket; 164—limiting plate;
170—elastic member;
200—a surface layer of the skin;
300—ink.

DETAILED DESCRIPTION

The technical solutions of the embodiments of the present disclosure will be described clearly and completely in the following by referring to the accompanying drawings. Obviously, the described embodiments show only a part of but not all of the embodiments of the present disclosure. All other embodiments obtained, based on the embodiments of the present disclosure, by any ordinary skilled person in the art without making creative work shall fall within the scope of the present disclosure.

In the description of the present disclosure, it is to be understood that any orientation or positional relationship indicated by the terms "top", "bottom", "top", "bottom", "inside", "outside", and so on, is an orientation or a positional relationship as shown in the accompanying drawings. The terms are used only to facilitate and simplify the description of the present disclosure, but do not indicate or imply that the device or element referred to must have a particular orientation or must be constructed and operated in a particular orientation. Therefore, the terms cannot be interpreted as limiting the present disclosure. In the present disclosure, the term "a plurality of" means two or more, unless otherwise expressly and specifically limited.

In the present disclosure, unless otherwise expressly provided and limited, the terms "mounted", "connected", "coupled", "fixed", and so on, shall be understood in a broad sense. For example, connection may be fixed connection, detachable connection, or two elements being configured as a one-piece structure; or may be mechanical connection or electrical connection; or may be direct connection, indirect connection through an intermediate medium, or two elements being internally connected or being interactive with each other. Any ordinary skilled person in the art shall understand specific meanings of the above terms in the present disclosure in a case-by-case manner.

The present disclosure will be illustrated in the following by referring to the drawings and the embodiments.

Figure 22A:
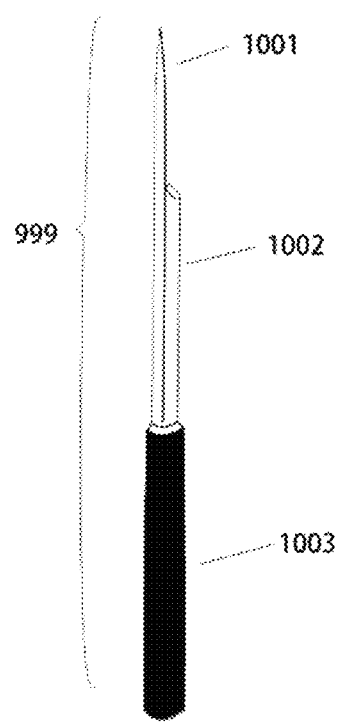
FIG. 22(a) is a structural schematic view of a single needle device.
Figure 22B:
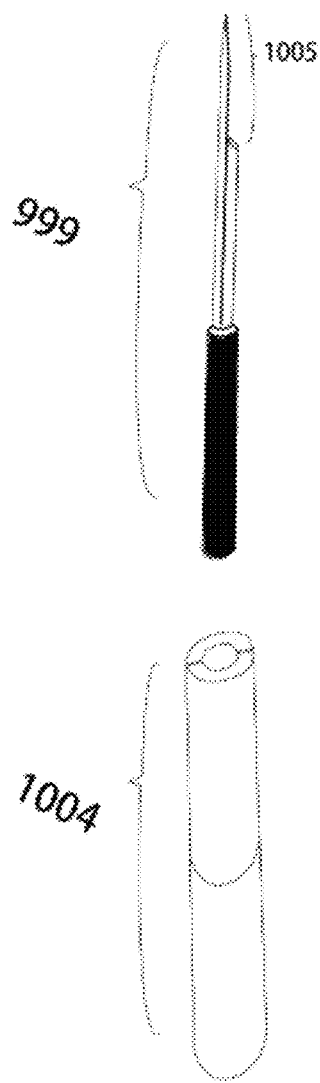
FIG. 22(b) is a schematic view of the single needle device shown in FIG. 22(a) being separated from a tattoo rod.

In order to perform fine colouring on a small area on the skin, for a tattoo device in the art, a single metal needle filament has a sharpened tip, serving as an operating end, and the single needle filament is welded to a needle handle. Further, the needle handle is secured, through a fixation end of the needle handle, to a tattoo rod. In this way, a single needle device is formed. As shown in FIG. 22(a), FIG. 22(a) shows a structural schematic view of the single needle device. The single needle device 999 includes a metal needle filament 1001, a needle handle 1002, a fixation end 1003 of the needle handle, a tattoo rod 1004, and a needle tip portion 1005. The single needle device 999 of FIG. 22(a) includes the single metal needle filament 1001 having a sharpened end, the needle handle 1002, the fixation end 1003 of the needle handle, the tattoo rod 1004, and the needle tip portion 1005. The needle tip portion 1005 is a part of the sharpened end of the single metal needle filament and protrudes from the needle handle. A length of the needle tip of the single needle device in the art is in a range from 3 mm to 10 mm. The needle tip 1005 of the single needle device 999 in the present embodiment is 3 mm. FIG. 22(b) is a schematic view of the single needle device shown in FIG. 22(a) being separated from a tattoo rod.

In an embodiment, the above single needle device may be taken to perform point-pricking to colour the skin. The point-pricking refers to the device repetitively pricking single points of the skin to bring the pigment into the skin. Alternatively, the above single needle device may be taken to draw lines to the colour the skin. Drawing lines to the colour the skin refers to the device breaking the skin from a single point and subsequently streaking the skin to bring the pigment into the skin. Although a process of manufacturing the single needle device in the art may be simple and the single needle device may be easily produced, the operating end of the single needle device in the art may cause the following colouring and safety problems. While colouring the skin to produce the tattoo, the operating end may prick the skin to reach an excessively large depth, and in this case, the pigments may spread outside a target colour area under the skin. Therefore, the pigment may be unable to be completely metabolized for several years, also known as "colour fading" in the tattoo industry.

According to scientific data, an average thickness of the epidermis of the human face is in a range from 0.2 mm to 1.0 mm, an average thickness of the epidermis at the eyebrow region is 0.5 mm, and an average thickness of the epidermis at the eyelid region is 0.33 mm. A thickness of one piece of conventional A4 paper of 80 g is 0.11 mm. That is, a thickness of the epidermis at the relatively thinner region of the human face is approximately equal to thicknesses of 2 to 3 pieces of conventional A4 paper. It may be difficult to control, based on subjective experience, a depth that is reached by the single needle device in the art piercing into the skin having the above thickness. By analyzing a large number of cases, "colour fading" cases may occur highly frequently, and this is because a piercing depth of the single needle device of the tattoo tool in the art may not be limited effectively, and a large error may be resulted due to the piercing depth being controlled by subjective determination of the operator only. Therefore, the piercing depth of tattoo may be determined and controlled in advance according to the thickness of the epidermis of various operating regions, such that a bleeding rate may be reduced to prevent occurrence of "colour fading".

According to accumulated data from the industry and experimental analysis, when the skin at the eyebrow region is pierced for a depth of 0.05 mm to 1.0 mm, the pigment may be retained at the skin for 3 months to 10 years in average. As the skin is pierced more deeply, the pigment may be retained longer. When the piercing depth is more than 1.0 mm, an average time length that the colour can be retained is more than 10 years. In the art, semi-permanent tattoo is the main demand in the market. The semi-permanent tattoo refers to the colour being retained for 1-2 years, and the piercing depth into the skin shall be controlled in the range of 0.3 mm to 0.6 mm, i.e., approximately thicknesses of 2-4 pieces of conventional A4 paper, each in the weight of 80 g.

In order to verify a relationship between the depth that the single needle device pierces into the skin and the time length that the colour is retained, a following verification experiment is performed.

For the tattoo tool in the art, a single needle device in a commonly used model (i.e., a diameter of the needle filament is 0.30 mm, a length of the needle tip is 3 mm) is taken to perform various pricking tests. For each of the various pricking tests, the single needle device is taken to prick a simulated silicone skin, and all simulated silicone skins applied in the various pricking tests are in a same specification. For the various pricking tests, an average height that the needle tip leaves the simulated silicone skin is 5 mm, and the needle tip pricks the simulated silicone skin twice per second in average. When an average depth that the needle tip pierces into the simulated silicone skin is 0.7 mm, approximately 0.06 kg force is applied to achieve the average depth. When an average depth that the needle tip pierces into the simulated silicone skin is 0.3 mm, approximately 0.04 kg force is applied to achieve the average depth. That is, that is, a difference of 0.02 kg force causes a 0.4 mm error in the depth that the needle tip pierces into the simulated silicone skin. The difference of 0.02 kg force is equivalent to a weight of 4-5 pieces of conventional A4 paper. It may be difficult to achieve this precision subjectively by human experience. For example, at the eyebrow region, when the depth that the skin is pierced is in a range of 0.3 mm to 0.6 mm, the colour may be retained to for 1-2 years. The error of only 0.02 kg force may cause the needle tip to pierce into the skin excessively deeply, resulting in the colour bing retained for an excessively long period of time. Therefore, the main demand of retaining the colour in the skin for 1-2 years may not be met, customer complaints may be caused easily.

Therefore, the depth that the single needle device of the tattoo tool in the art pierces into the skin cannot be precisely controlled, causing the "colour fading" problems. Further, the depth that the single needle device pierces into the skin is closely related to the time length that the pigment is retained in the skin. An effect of the tattoo may be affected since depths of various piercings are inconsistent and not controllable.

In order to solve deficiencies of the single needle device in the art, the present disclosure provides a tattoo needle, wherein the depth that the tattoo needle may pierce into the skin may be accurately defined in advance, such that the tattoo needle may be prevented from piercing into the skin excessively deeply, and therefore, the pigments may be prevented from spreading to a non-target colouring region.

A specific structure of the introduction needle provided by the present disclosure will be described in detail below by referring to the accompanying drawings.

Embodiment 1

As shown in FIG. 1(a) to FIG. 1(d), in an embodiment, an introduction needle 100 may include a liquid guiding member 110 and a needle piercing portion 140 disposed at an end of the liquid guiding member 110. The needle piercing portion 140 includes a piercing projection 141. The piercing projection 141 includes a substrate 1411 and a single needle tooth 1412. The needle tooth 1412 is fixedly arranged on an end face of the substrate 1411. A central axis of the needle tooth 1412 is perpendicular to the end face of the substrate 1411. When the needle is piercing the skin, the substrate 1411 may limit a depth that the needle pierces the skin. The substrate 1411 presses against the skin to limit the depth that the needle tooth 1412 pierces into the skin. The liquid guiding member 110 may be columnar. The other end face of the substrate 1411 is fixed to an end of the columnar liquid guiding member 110. A central axis of the columnar liquid guiding member 110 is parallel to the central axis of the needle tooth 1412. The structure of the introduction needle 100 may be similar to a pen. The liquid guiding member 110 may be similar to a barrel of the pen. The needle piercing portion 140 may be similar to a tip of the pen. The liquid guiding member 110 may pierce the skin in the vertical direction, ensuring that a piercing position may not be shifted, the needle tip may not slip, and a redundant wound may not be generated.

As shown in FIG. 1(a) to FIG. 1(d), in an embodiment, the liquid guiding member 110 may include a liquid guiding post 111 and a connecting rod 112 connected to the liquid guiding post 111. That is, the liquid guiding member 110 includes two parts, one of the two parts guides ink to flow, and the other one of the two parts is configured for connection and driving. The connecting rod 112 is connected to a drive portion. The liquid guiding member 110 reciprocates, driven by the drive portion, along the central axis of the liquid guiding member 110. In a case, the drive portion may be a motorized rod, and that is, the connecting rod 112 of the liquid guiding member 110 is directly connected to the motorized rod (which may be fixed connection or a non-fixed connection (including abutting connection, hanging connection, and contact connection)). The motorized rod directly drives the liquid guiding member 110 to move. In another case, the drive portion may be an elastic member 170, such as a spring. The connecting rod 112 of the liquid guiding member 110 is connected to an end of the spring. A case (or a member fixedly connected to the case) is connected to the other end of the spring. Further, an external force is applied to drive the spring to be deformed. When the liquid guiding member 110 is moving along an axial direction of the case 150 towards a needle outlet end, the liquid guiding member 110 may be reset by a force from the deformed elastic member, such that the liquid guiding member 110 moves reciprocately within the case 150. In still another case, an operator may also hold the connecting rod 112 by hand to directly tattoo.

Figure 3A:
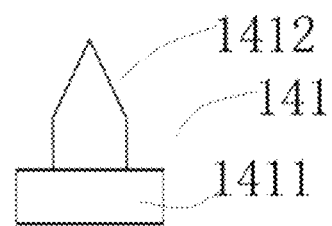
FIG. 3(a) is a front view of the piercing projection according to an embodiment of the present disclosure.
Figure 3B:
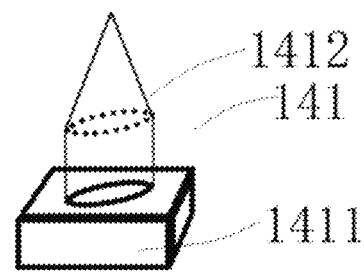
FIG. 3(b) is a perspective view of the piercing projection shown in FIG. 3(a).
Figure 3C:
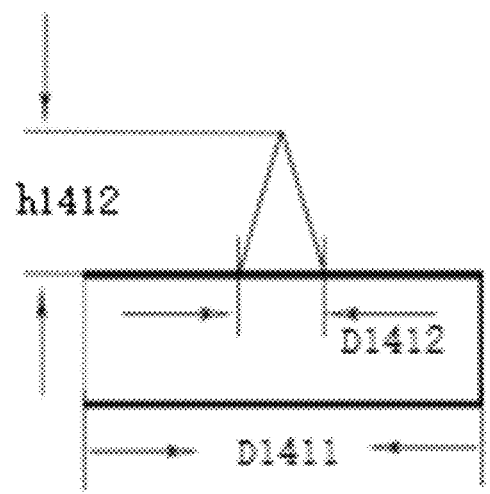
FIG. 3(c) is a front view of the piercing projection according to another embodiment of the present disclosure.
Figure 3D:
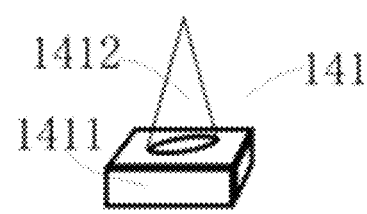
FIG. 3(d) is a perspective view of the piercing projection shown in FIG. 3(c).

In order to achieve various tattoo patterns and tattoo positions, the present embodiment provides a piercing projection 141, as shown in FIG. 3(d). The piercing projection 141 may include a substrate 1411 and a needle tooth 1412 arranged on the substrate 1411. The substrate 1411 serves as a depth limiting plate to limit a depth that the needle tooth 1412 pierces into the skin. The substrate 1411 and the needle tooth 1412 may be configured as a one-piece and integral structure, or configured as separated elements being fixedly connected with each other. When the substrate 1411 and the needle tooth 1412 are configured as the one-piece and integral structure, connection strength and stability of the needle tooth 1412 may be enhanced. Further, safety of the needle tooth 1412 may be improved while the needle tooth 1412 is piercing the skin. The one-piece and integral structure may be suitable for a high frequency piercing process.

The advantages of the introduction needle in the present disclosure, compared to the single needle device in the art, will be illustrated below by referring to FIGS. 23(a), 23(b), 24(a), and 24(b).

Figure 23A:
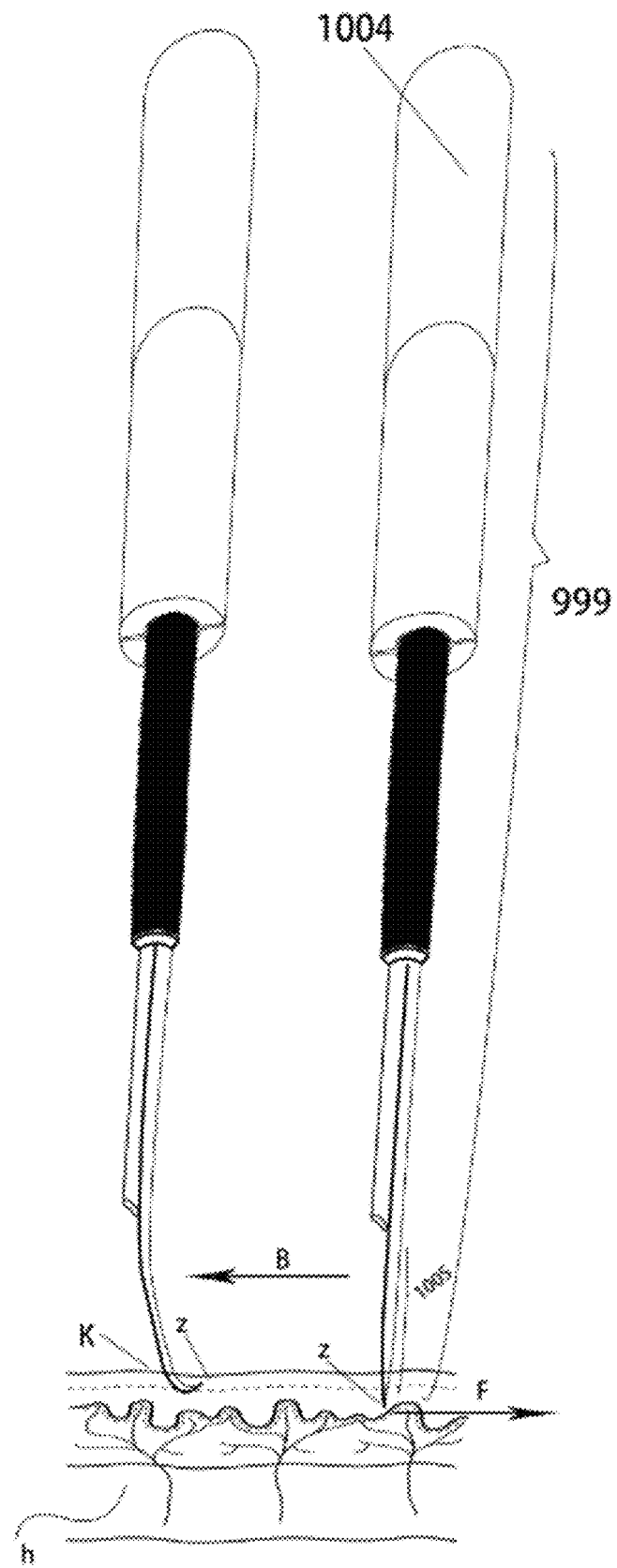
FIG. 23(a) is a cross-sectional of piercing a single needle device in the art into the skin.
Figure 23B:
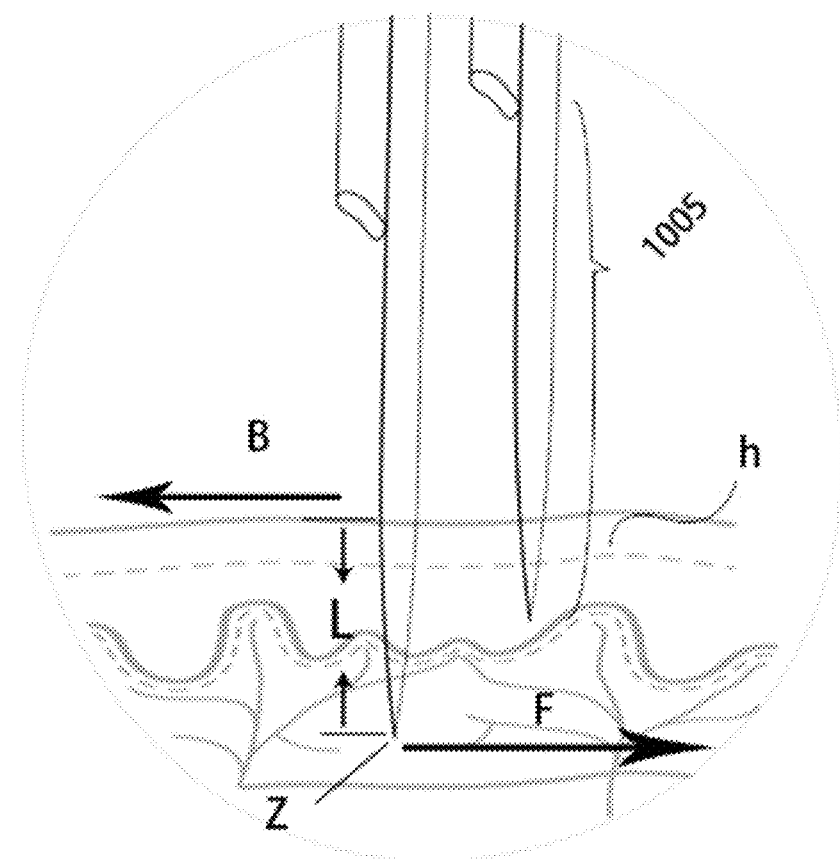
FIG. 23(b) is a schematic view of a force applied to a tip of the metal needle filament of the single needle device in the art, as shown in FIG. 34(a), while the single needle device is piercing into the skin.

As shown in FIG. 23(a), a cross-sectional structure of the skin is noted as h. The single needle device 999 of the tattoo tool in the art is connected to the tattoo rod 1004. The operator may hold the tattoo rod 1004 by hand to repetitively streak the skin along a direction indicated by an arrow B to colour the skin. A front end Z of the needle tip 1005 is under the skin and may be subjected to a resistance force F in a direction opposite to the direction B. The front end Z of the needle tip 1005 may be bent, as shown at K. Further, as shown in FIG. 23(b), the front end Z of the needle tip 1005 under the skin may be bent because of a force moment. The force moment=force arm*force (M=L*F). In a case that all forces in the horizontal direction are the same, as the needle tip pierces into the skin more deeply, the force arm L is larger, and the force moment M applied to the front end Z of the needle tip 1005 is larger. Therefore, the front end Z of the needle tip 1005 may be bent more easily. Therefore, the introduction needle provided by the present disclosure may limit the depth that the needle tip pierces into the skin, and that is, a maximum moment applied to the needle tip is limited, and the needle tip may be prevented from being bent.

Figure 24A:
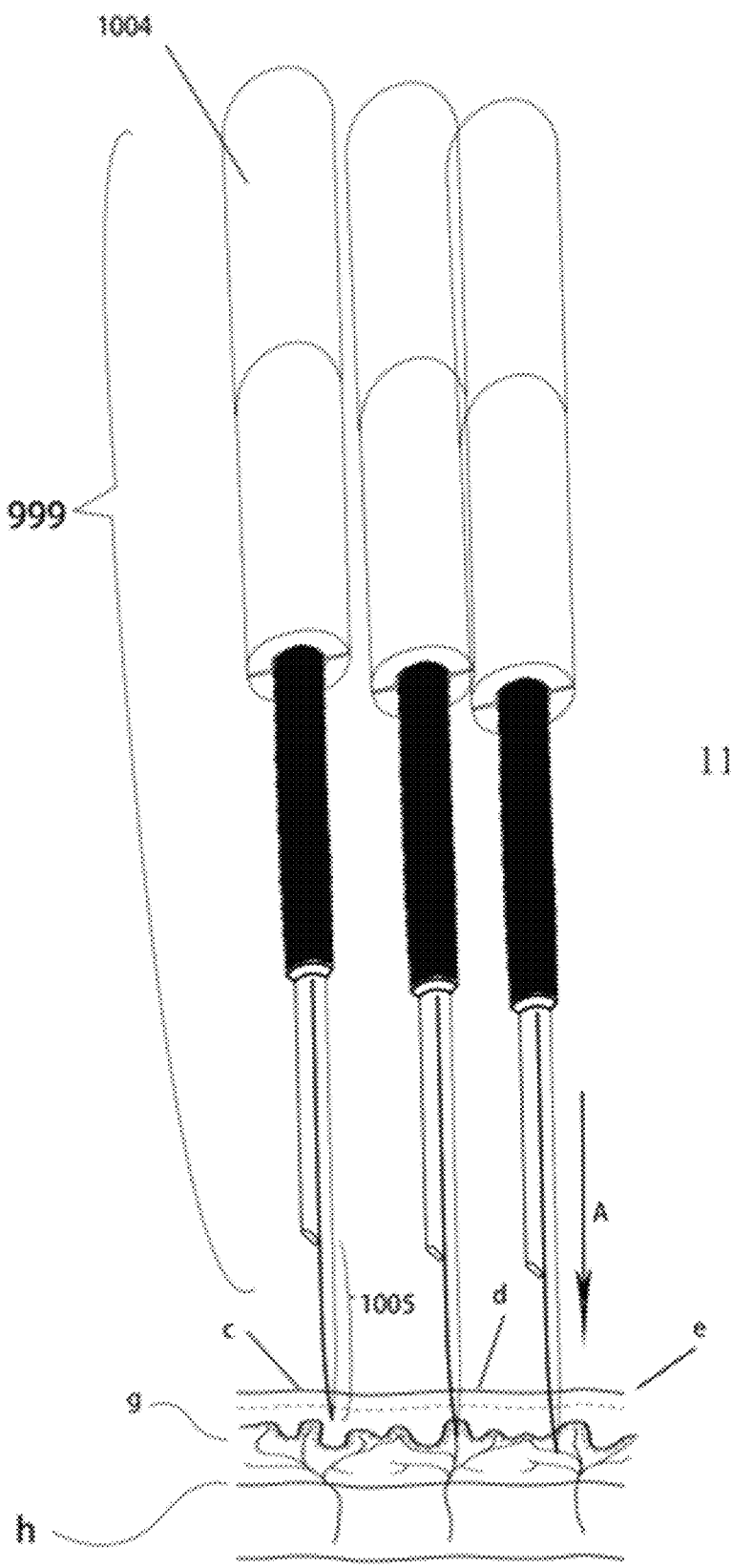
FIG. 24(a) is a cross-sectional view of the single needle device in the art piercing into the skin.

As shown in FIG. 24(a), the cross-sectional structure of the skin is noted as h, and subcutaneous blood vessels are noted as g. The operator holds the tattoo rod 1004 by hand to repeatedly prick the skin along the arrow A in an up-down direction to colour the skin. The needle tip 1005 pierces into the skin to reach position as indicated by c, d, and e, in FIG.

Figure 24B:
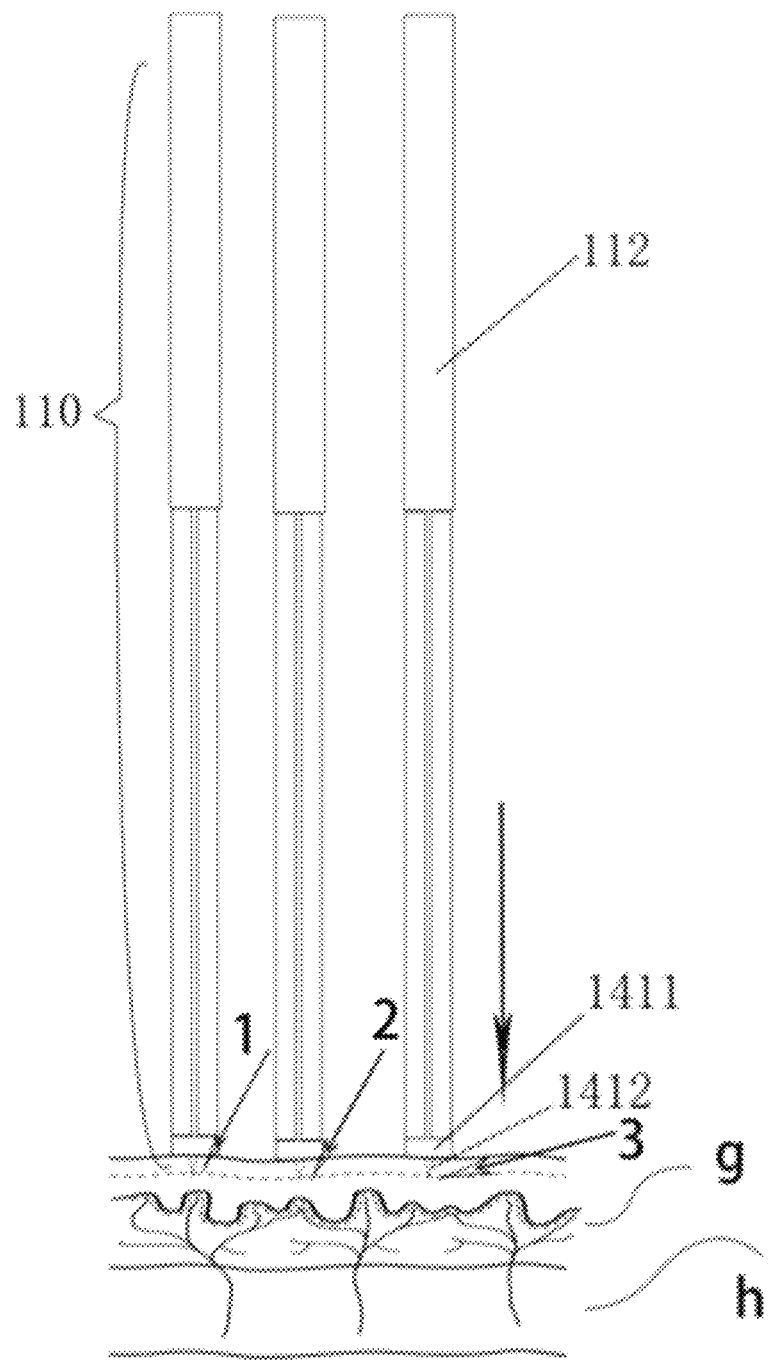
FIG. 24(b) is a cross-sectional view of the single needle device, according to an embodiment of the present disclosure, piercing into the skin.

24(a), and the position c, d, and e refer to different depths under the skin. The depths of the positions d and e show that the needle tip has reached locations at which the subcutaneous blood vessels are located. As shown in FIG. 24(b), the operator may alternatively directly hold the connecting rod 112 to repeatedly prick the skin to colour the skin. The needle tooth 1412 having a predetermined piercing length pierces into the skin, and the substrate 1411 contacts the skin to form a barrier, such that the piercing depth is limited. As indicated by points 1, 2, and 3 shown in FIG. 24(b), the piercing depths are controllable and are consistent. A height of the needle tooth 1412 is predetermined within a certain range to prevent the subcutaneous blood vessels from being pierced and to prevent the tip from being bent due to an excessive large force moment.

Embodiment 2

As shown in FIG. 3(c) to FIG. 3(d), in an embodiment, the needle tooth 1412 of the present disclosure may be a protrusion protruding from the substrate 1411. A size of a cross sectional area of the protrusion decreases along a direction that the needle teeth piece into the skin. For example, the size of the cross sectional area of the protrusion decreases in a direction from the substrate 1411 towards a free end of the protrusion. A bottom of the needle tooth is connected to the substrate 1411, and the free end of the needle tooth is a top end. Based on repeated experiments, in order to achieve a better effect of guiding the pigments, a height range h1412 of the needle tooth is 50 µm≤h1412≤1500 µm, and a diameter range D1412 of the bottom of the needle teeth is 50 µm≤D1412≤twice the height of the needle tooth, in general, D1412≤h1412.

In an embodiment, the substrate 1411 is in an arbitrary polygonal shape. The needle tooth 1412 is disposed on an end face of the substrate 1411. In order to achieve the better effect of guiding the pigments, a minimum edge length of the substrate 1411 is recorded as D1411. In the case D1411>D1412, the pigments may flow to reach the substrate 1411 from the relatively thick liquid guiding post 111 and may further be guided from the substrate to the needle tooth 1412.

Figure 4A:
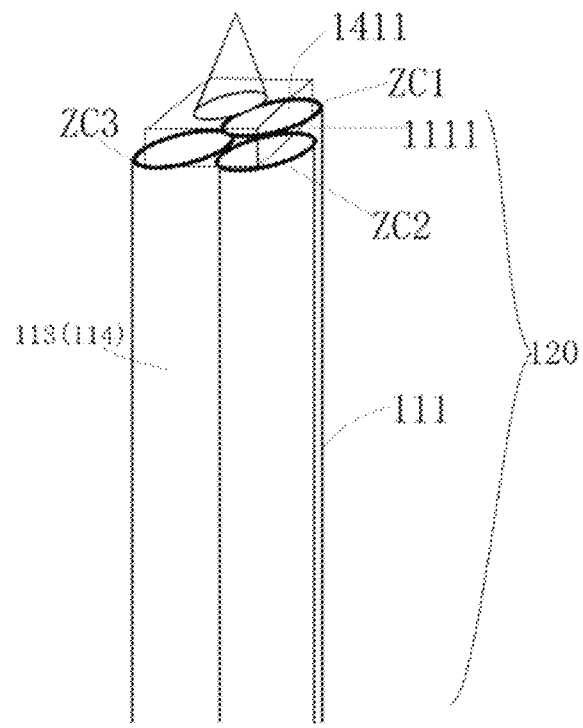
FIG. 4(a) is a perspective view of a portion of the introduction needle according to an embodiment of the present disclosure.
Figure 4B:
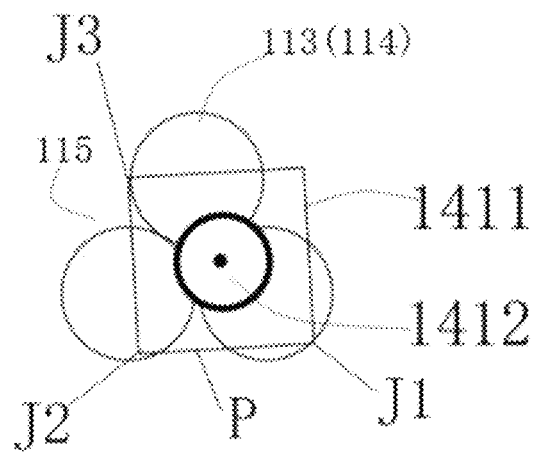
FIG. 4(b) is a schematic view of the introduction needle shown in FIG. 4(a), viewed from a viewing angle.
Figure 4C:
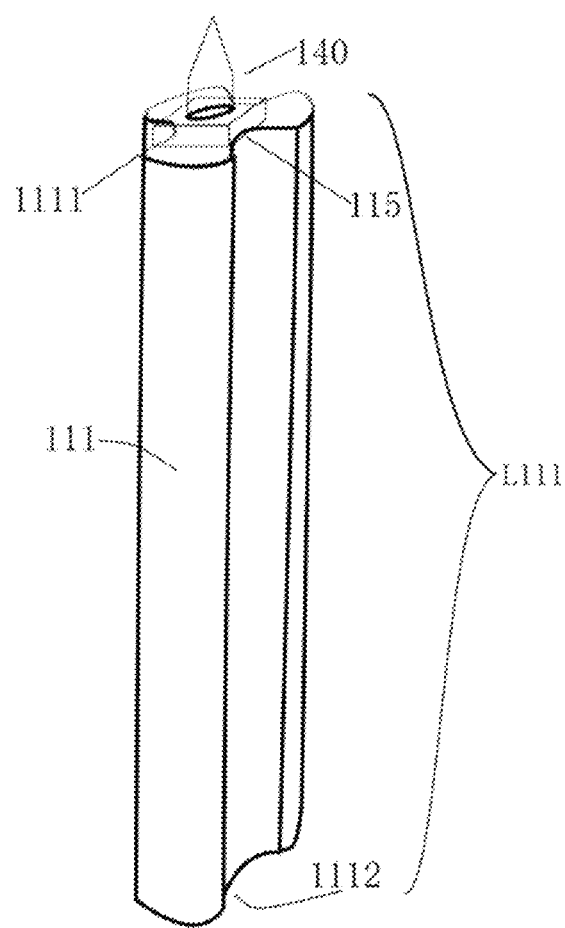
FIG. 4(c) is a perspective view of a portion of the introduction needle according to another embodiment of the present disclosure.
Figure 4D:
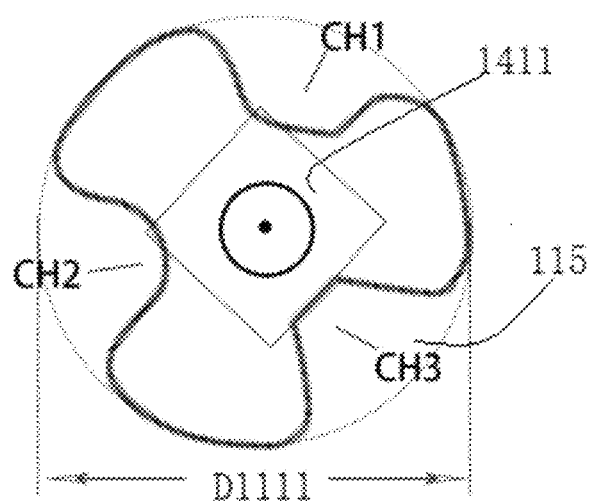
FIG. 4(d) is a schematic view of the introduction needle shown in FIG. 4(c), viewed from a viewing angle.

As shown in FIG. 4(d), a diameter of a first end face 1111 of the liquid guiding post 111 is D1111. Based on repeated experiments, in order to achieve the better effect of guiding the pigments and to have a certain extent of rigidity, 180 µm≤D1111≤1800 µm, and D1111>D1411. Further as shown in FIG. 4(c) and FIG. 4(d), three channels 115 are defined in the liquid guiding post 111 (CH1, CH2, and CH3 in FIG. 4(c) each represents one of the three channels). As shown in FIG. 4(c), a length of the liquid guiding post 111 is L111, and L111>D1111. In an embodiment, in order to allow the device to carry an increased amount of ink and to release the ink continuously and slowly, L111>2×D1111. That is, the length of the liquid guiding post 111 is greater than two times of the diameter of the first end face of the liquid guiding post 111. Of course, a cross section of the piercing projection 141, taken by the substrate 1411, may be arbitrary polygonal, for example, the cross section may be triangular, quadrilateral, pentagonal, or in other regular or irregular polygonal shapes. When the shape of the substrate 1411 is arbitrary polygonal, an axial length of the liquid guiding post 111 is at least two times of the length of the shortest edge of the first end face 1111 of the liquid guiding post 111, and the axial length of the liquid guiding post 111 is greater than a length of the longest edge of the first end face 1111.

Figure 5A:
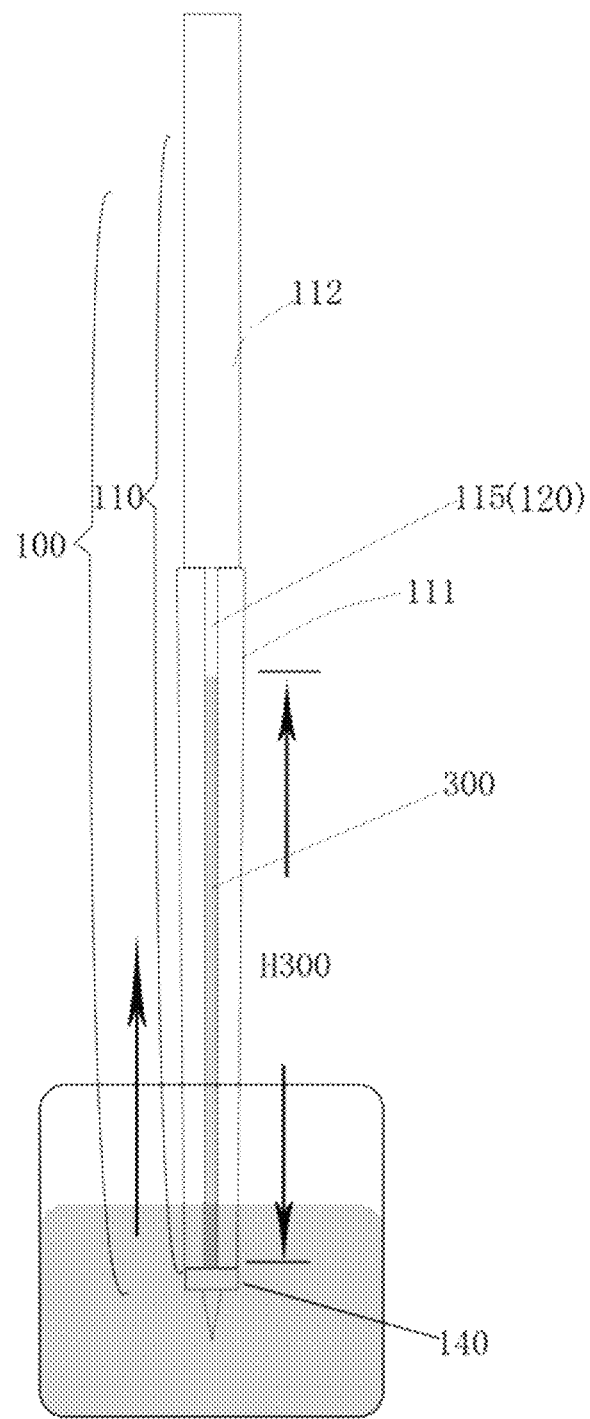
FIG. 5(a) is a schematic view showing a state of the introduction needle while the introduction needle is intaking ink, according to an embodiment of the present disclosure.

As shown in FIG. 5(a), the liquid guiding member 110 is arranged with a capillary liquid storage unit 120. A channel 115 in the capillary liquid storage unit 120 is defined in an outer wall of the liquid guiding member 110. Further, a capillary principle is applied to enable the channel 115 to store the pigments (the pigments and the ink in the present disclosure both refer to dyes that can colour the skin). The needle piercing portion 140 of the introduction needle 100 and a bottom of the channel 115 are submerged into the pigments, and the pigments rises along the channel 115 against the gravity. In this case, the channel 115 serves as a capillary liquid storage unit 120 that can temporarily store the pigments. When the introduction needle that has adsorbed the pigments is being used, the capillary liquid storage unit may continuously supply ink to the needle tooth of the needle piercing portion. When the liquid guiding member 110 is dipped into the pigments to intake the pigments, the pigments rises along the capillary liquid storage unit 120 to form a pigment column. For simple illustration, a height of the pigment column is recorded as H300.

Figure 5B:
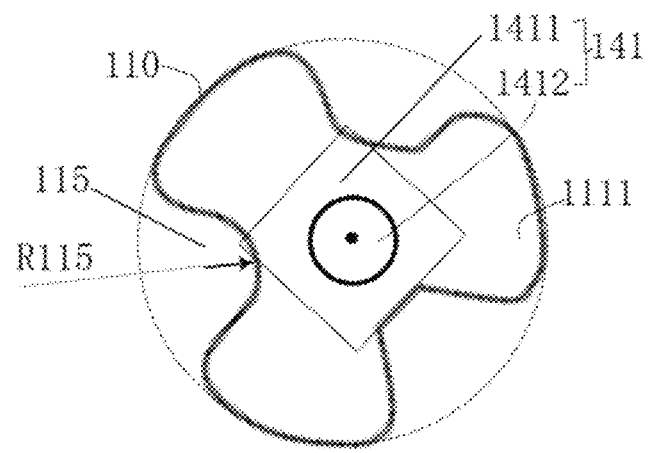
FIG. 5(b) is a top view of the introduction needle shown in FIG. 5(a), viewed from a viewing angle.

As shown in FIG. 5(b), the piercing projection 141 is fixed to the first end face 1111 of the liquid guiding member 110, and a radius of the channel 115 in the outer wall of the liquid guiding member 110 may be recorded as R115.

By collecting and analyzing data, a density of the pigments in the art at room temperature is about 0.7-1.31 g/ml, and a surface tension of the pigments at the room temperature is almost equal to a surface tension of water, which is about 72 mN/m. A capillary formula is as follows: a height h that the liquid rises along a capillary tube=2*surface tension coefficient*cos θ/(density of the liquid*gravitational acceleration g*radius of the capillary tube r). The θ is an angle between a liquid surface and a wall of the capillary tube. The radius of the channel R115 of the liquid storage unit 120 corresponds to the radius of the capillary tuber in the capillary formula. According to the experimental test and verification of the capillary formula, as a value of the R115 is reduced, a value of the H300 is increased. That is, as the channel of the capillary liquid storage unit 120 is thinner, the height of the pigment column H300 is higher, and more pigments may be carried. Therefore, the needle may not dip the pigments frequently, the tattooing may be performed continuously and efficiently.

Figure 5C:
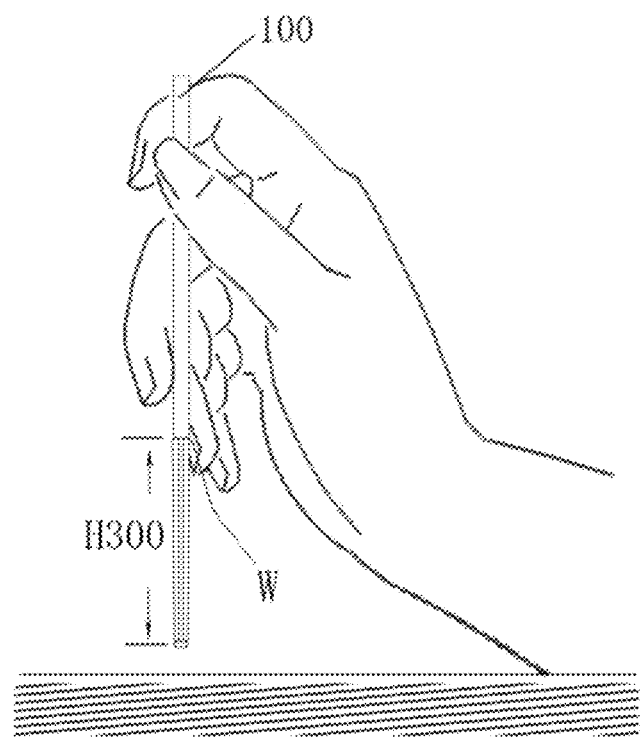
FIG. 5(c) is a schematic view showing a state of the introduction needle in FIG. 5(a), which has intaken the ink, piercing into the skin, according to an embodiment of the present disclosure.
Figure 6:
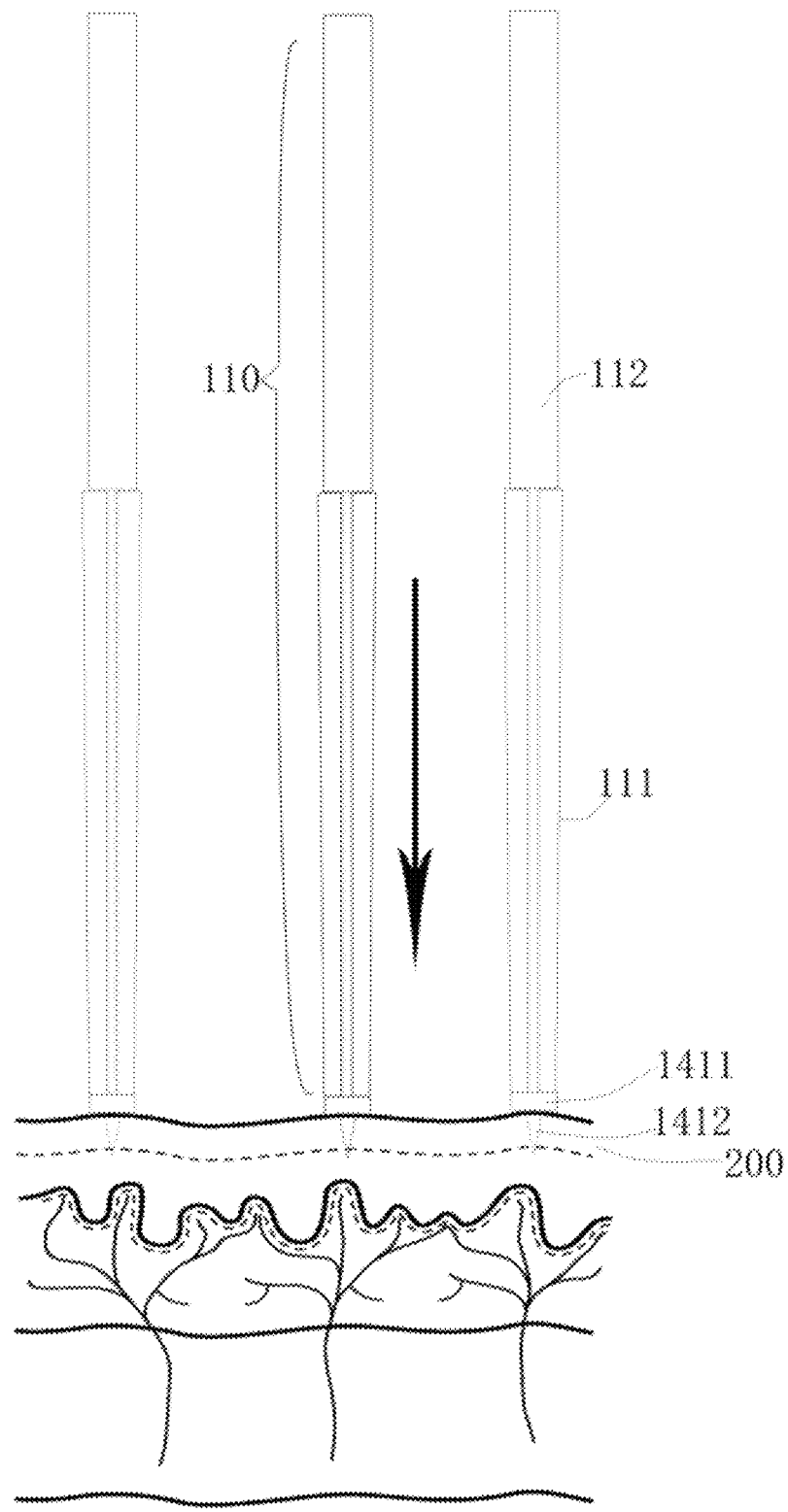
FIG. 6 is a schematic view showing a state of the introduction needle piercing into the skin according to an embodiment of the present disclosure.

In an embodiment, the liquid guiding member 110 of the introduction needle 100 is made of polycarbonate. Based on precision of the main production process in the art, the radius of the channel of the capillary liquid storage unit 120 may be made to have a precision of 0.1 mm, and the height of the pigment column H300 may be more than 100 mm. However, as shown in FIG. 5(c), according to a conventional way that the operator holds the introduction needle 100 by hand and a measurement of dimensions of a general human hand, a lowest position W of the introduction needle 100 that is held by the hand is generally not more than 50 mm from the needle tip. Therefore, the height H300 of the channel of the capillary liquid storage unit 120 arranged on the introduction needle 100 in the present embodiment is <50 mm.

Figure 2:
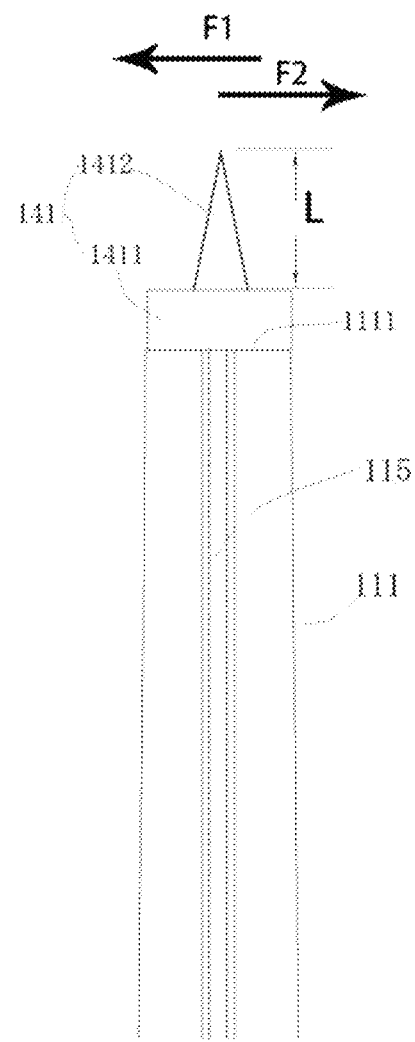
FIG. 2 is a structural schematic view of a liquid guiding post and a piercing projection according to an embodiment of the present disclosure.
Figure 4E:
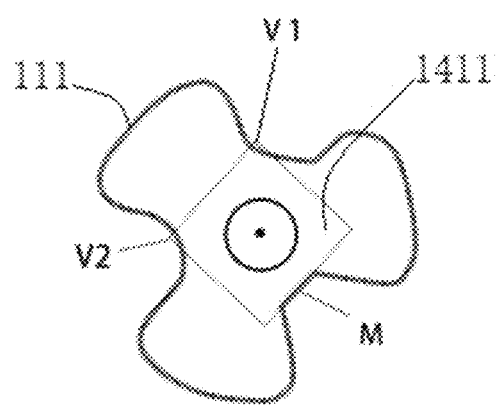
FIG. 4(e) is a schematic view of the introduction needle according to another embodiment of the present disclosure.

As shown in FIG. 2, in an embodiment, in order to achieve the better effect of guiding the pigments, the liquid guiding post 111 is fixed, by adhering, to the substrate 1411 of the piercing projection 141. As shown in FIG. 4(e), at least one corner V1, V2, and/or an edge M of the substrate 1411 on which the piercing projection 1411 is arranged is aligned with (infinitely approach) an edge of the outer wall of the liquid guiding post 111.

In an embodiment, the substrate 1411 of the piercing projection 141 is disposed at a middle of an end face of the liquid guiding member 110, and a distance from the edge of the outer wall of the liquid guiding member to one corner or one edge of the substrate is not more than 0.18 mm. That is, in an embodiment, the substrate may be disposed at a center of the first end face. However, in order to achieve the better effect of guiding the pigments, a distance from the edge of the outer wall of the liquid guiding member to one corner or one edge of the substrate is not more than 0.18 mm.

As shown in FIG. 7(*a*), for the introduction needle in the present embodiment an adhesive seam is defined between the liquid guiding member 110 and the piercing projection 141. After use, the introduction needle 100 may be functionally destroyed by separating, by any sharp instrument, the liquid guiding member 110 from the piercing projection 141.

Embodiment 3

In an embodiment, FIG. 1(*a*) shows an introduction needle 100, and a depth that the introduction needle 100 pierces into the skin from a single point, may be accurately predefined. The introduction needle 100 includes a liquid guiding member 110, a needle piercing portion 140, and a channel 115 defined in an outer wall of the liquid guiding member 110. The channel 115 serves as a capillary liquid storage unit 120.

In an embodiment, as shown in FIG. 4(*a*), the liquid guiding post 111 includes three metal filaments ZC1, ZC22, and ZC3 that are cut flat. The metal filaments ZC1, ZC22, ZC3 are adjacent to each other and are not fixedly connected to each other. A gap between the filaments has a capillary effect and serves as the capillary liquid storage unit. In an embodiment, the liquid guiding post 111 is fixedly connected to the connecting rod 112. The liquid guiding post 111 is welded and fixed to the substrate 1411 of the piercing projection 141.

In an embodiment, as shown in FIG. 3(*a*) and FIG. 3(*b*), the needle tooth 1412 of the present disclosure includes a tail pin and a top pin integrally formed with an end of the tail pin. The tail pin may be columnar, and the top pin may be protruding from the tail pin. A size of a cross sectional area of the top pin decreases in a direction extending from the tail pin to a free end of the top pin away from the tail pin, and the other end of the columnar tail pin is fixedly connected to the substrate.

In an embodiment, as shown in FIG. 4(*b*), the edge of the outer wall of the liquid guiding post 111 is aligned with (indefinitely approach) at least one corner J1, J2, J3 of the substrate 1411 and/or with one edge P of the substrate 1411.

In an embodiment, the liquid guiding post 111 is welded and fixed to the piercing projection 141 of the introduction needle 100, in the present embodiment. The piercing projection 141 is made of monocrystalline silicon. After usage, the introduction needle 100 may be functionally destroyed by knocking, by any sharp instrument, off the needle tooth 1412. The destroyed introduction needle may be shown as FIG. 7(*b*).

FIG. 1(*d*) shows an introduction needle 100, and a depth that the introduction needle 100 pierces into the skin from a single point, may be accurately predefined. The introduction needle 100 includes a piercing projection 141, a liquid guiding post 111, and a capillary liquid storage unit 120. The piercing projection 141 includes one needle tooth 1412 and a substrate 1411. A depth that the needle tooth 1412 pierces into the skin may be predefined, and the needle tooth 1412 is mounted on the substrate 1411. The needle tooth 1412 is a protrusion protruding from the substrate 1411. A size of a cross sectional area of the protrusion decreases along a direction that the needle teeth piece into the skin. For example, the size of the cross sectional area of the protrusion decreases in a direction from the substrate 1411 towards a free end of the protrusion. For example, the needle tooth may be conical. The substrate 1411 and the needle tooth 1412 are configured as a one-piece and integral structure. The substrate 1411 limits the depth that the needle tooth 1412 pierces into the skin. In an embodiment, as shown in FIG. 1(*d*), the liquid guiding post 111 is a strip. A fibrous substance may be attached to the outer wall of the liquid guiding post 111. A gap in a body of the fibrous substance and a gap between the body of the fibrous substance and the outer wall of the liquid guiding post 111 cooperatively serve as the capillary liquid storage unit 120.

Embodiment 4

As shown in FIG. 4(*c*), in an embodiment, the liquid guiding post 111 may have a first end face 1111 and a second end face 1112. The central axis of the liquid guiding column 111 extends through a center of the first end face 1111 and a center of the second end face 1112. The liquid guiding column 111 may be a column in any shape, such as a cylinder, a quadratic column, a cone-like column (or a circular truncated cone), an irregular column, and so on.

As shown in FIG. 1(*a*), a side face of the substrate 1411 is fixed to the first end face 1111 of the liquid guiding post 111 (the substrate may be adhered to and fixed to the first end face). The connecting rod 112 may be fixedly or detachably connected to the second end face 1112 of the liquid guiding post 111. The connecting rod 112 may be a column or in other shapes. The connecting rod 112 is substantially configured to connect the liquid guiding post 111 to the drive portion.

In an embodiment, a shape of the liquid guiding post 111 of the present disclosure may be arbitrary, as long as any one of the following conditions is met.

For a condition 1, a shape of the first end face 1111 is the same as a shape of the second end face 1112, and a size of the first end face 1111 is the same as a size of the second end face 1112.

For a condition 2, the shape of the first end face 1111 is the same as the shape of the second end face 1112, and the size of the first end face 1111 is less than the size of the second end face 1112.

For a condition 3, the shape of the first end face 1111 is different from the shape of the second end face 1112, and the size of the first end face 1111 is less than the size of the second end face 1112.

Based on the above conditions, the most basic characteristics of the liquid guiding member 110 is that the liquid guiding member 110 is a column. As long as the liquid guiding member 110, when being vertically disposed, may guide and direct liquid to flow, the shape of the liquid guiding member 110 is arbitrary. The shape of the liquid guiding member 110 may be determined based on the operator's demands. The accompanying drawings, which show that the shape is columnar and conical-like, are for illustrating the structure of the liquid guiding member only, and shall not be interpreted as limiting the shape of the shape of the liquid guiding member 110.

In an embodiment, the axial length of the liquid guiding post 111 is greater than a length of the longest edge or a diameter of a cross section of the first end face 1111 of the liquid guiding post 111. That is, the liquid guiding post 111 of the present disclosure is preferably an elongated column.

In an embodiment, the axial length of the liquid guiding post 111 is at least two times of the length of the shortest edge or the diameter of the first end face 1111 of the liquid guiding post 111, and the axial length of the liquid guiding post 111 is greater than the length of the longest edge or the diameter of the first end face 1111. When this length-to-diameter ratio is met, the shape of the liquid guiding member 110 is standardized, and the elongated liquid guiding member 110, when being vertically disposed, provides a better liquid guiding and storage effect.

Embodiment 5

In the tattoo process, the tattoo ink 300 (or dye) may be introduced into a superficial layer of the skin through the tattoo tool. The tattoo tool in the art may not adsorb, when being submerged into the ink 300, a large amount of ink 300. In a process that the tool pierces into the skin highly frequently, the amount of ink in the tattoo tool does not reach the amount of ink required for one piercing stage. Therefore, a high rate of empty needle during piercing may be caused. In order to improve the above mentioned defects of the tattoo tool in the art, the liquid guiding member 110 of the introduction needle in the present disclosure is improved to meet the amount of ink required for one tattoo process. The structure of the liquid guiding member 110 will be described in detail below.

As shown in FIG. 4(a) to FIG. 4(d), FIG. 5(a), and FIG. 6, the capillary liquid storage unit 120 is arranged in the liquid guiding post 111. Liquid stored in the capillary liquid storage unit 120 (under the gravitational force or other forces) is guided to flow to the needle piercing portion 140. The needle tooth 1412 pierces into the surface of the skin 200, and at the same time, the liquid is introduced into the surface of the skin 200 along the needle tooth 1412. The capillary liquid storage unit 120 may temporarily store the ink 300. The liquid guiding member 110 may be submerged in an ink bottle, and the capillary liquid storage unit 120 in the liquid guiding member 110 may adsorb and temporarily store the ink. When the liquid guiding member 110 carries the needle tooth 1412 of the needle piercing portion 140 to pierce into the skin, the ink 300 stored in the capillary liquid storage unit 120 is gradually guided to flow to the tip of the needle tooth 1412. In the present disclosure, the capillary liquid storage unit 120 is arranged to allow the liquid guiding member 110 to release the ink gradually, ensuring continuous supply of the ink and reducing a rate of empty needles.

Figure 7A:
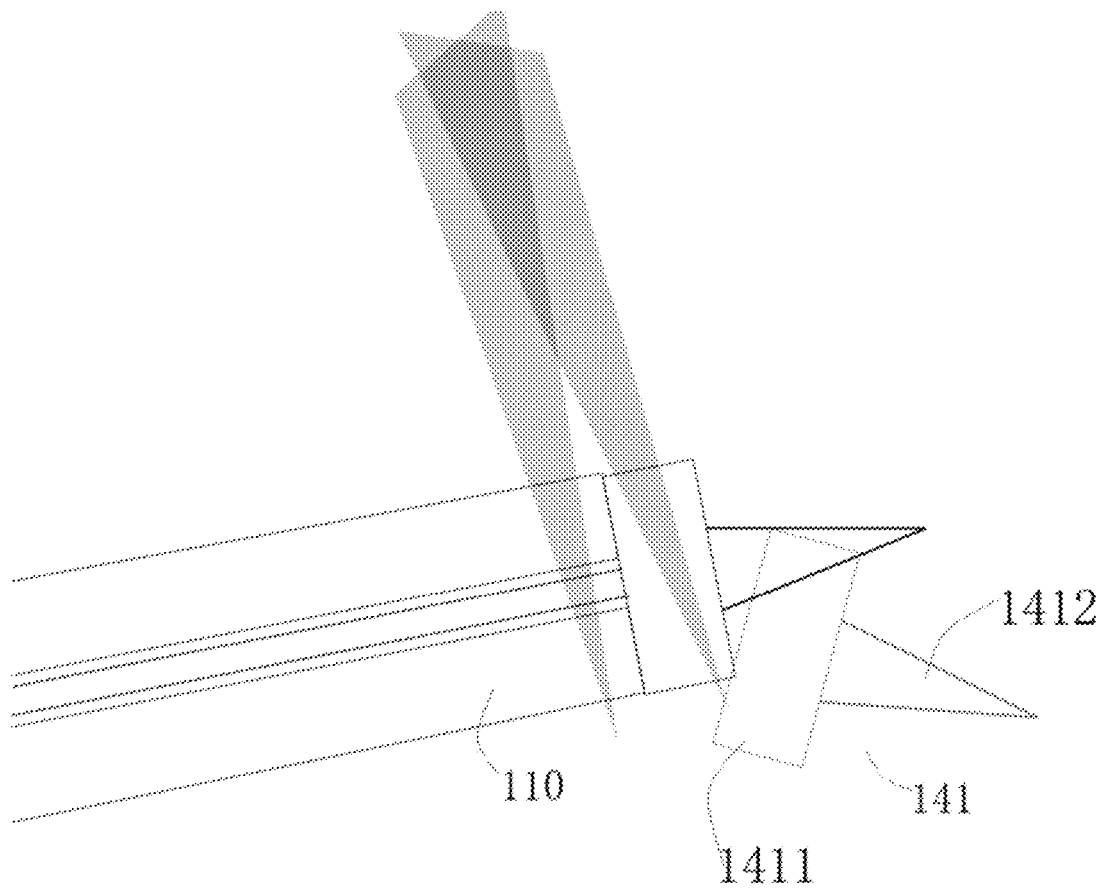
FIG. 7(a) is a schematic view showing a state of destroying an introduction needle after being used according to an embodiment of the present disclosure.
Figure 7B:
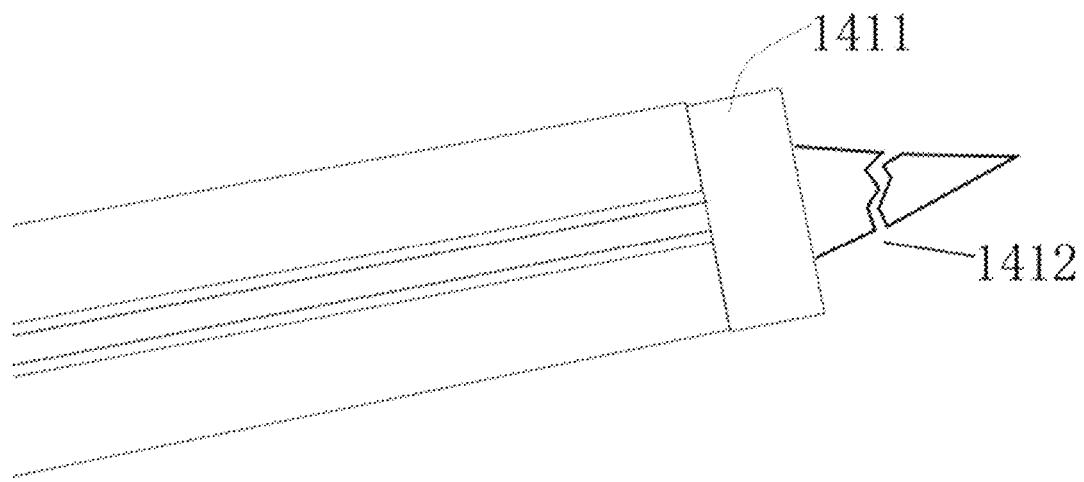
FIG. 7(b) is a schematic view showing a state of destroying an introduction needle after being used according to another embodiment of the present disclosure.

According to the above embodiments, the introduction needle is required to be break into the skin during the tattoo process. Therefore, the introduction needle that has been used needs to be destroyed to prevent microbial spread caused by secondary usage. The introduction needle provided by the present disclosure has taken this into account. Therefore, as shown in FIGS. 7(a) to 7(b), the needle tooth 1412 of the introduction needle are destroyed. Alternatively, the needle piercing portion of the introduction needle is directly destroyed, and the remaining liquid guiding post 111 may be further reused.

Figure 1B:
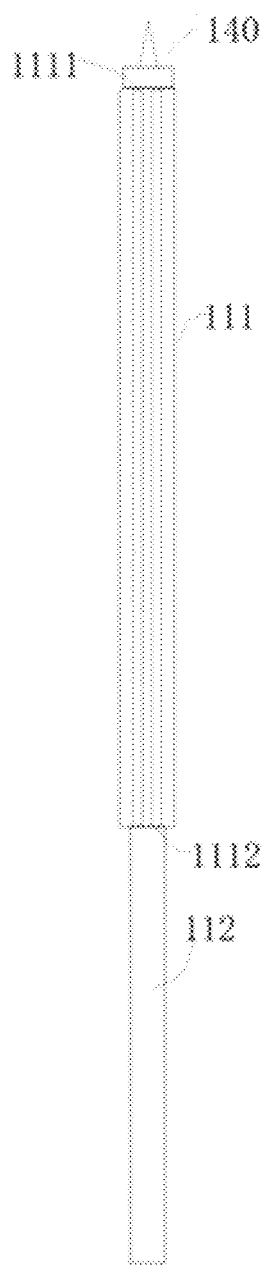
FIG. 1(b) is another structural schematic view of an introduction needle according to an embodiment of the present disclosure.
Figure 1C:
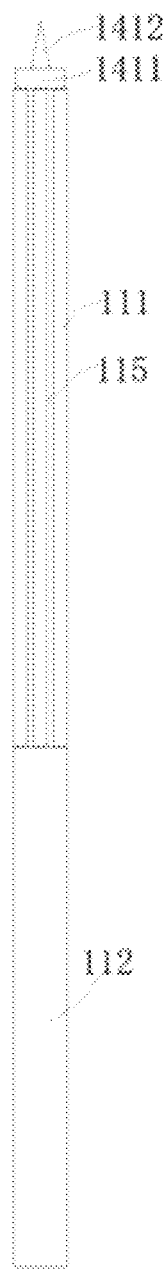
FIG. 1(c) is another structural schematic view of an introduction needle according to an embodiment of the present disclosure.

As shown in FIG. 1(a) to FIG. 1(c), in an embodiment, the liquid guiding post 111 of the present disclosure defines a plurality of channels 115. The plurality of channels 115 extend along the axial direction of the liquid guiding member 110 and are defined in the outer wall of the liquid guiding post 111 and/or at an interior of the liquid guiding post 111. The plurality of channels 115 cooperatively serve as the capillary liquid storage unit 120. The capillary liquid storage unit 120 is substantially configured to continuously supplying ink 300 to the tip of the needle tooth 1412. Therefore, at least one of the plurality of channels 115 temporarily stores the liquid, and the liquid in the at least one of the plurality of channels 115 may be guided by the gravitational force to flow to reach the needle tooth 1412 of the needle piercing portion 140. The plurality of channels 115 may be integrally defined in the outer wall of the liquid guiding member 110 by etching, cutting, engraving and grinding, or injection molding.

As shown in FIG. 1(a) to FIG. 1(c), in an embodiment, the plurality of channels 115 are arranged on the outer wall of the liquid guiding post 111. The plurality of channels 115 serve as the capillary liquid storage unit 120. The plurality of channels 115 in the present embodiment may be objects, such as a needle filament or a needle tube, that are connected to the liquid guiding post 111 and may form a gap.

As shown in FIG. 4(a) to FIG. 4(b), in an embodiment, the liquid guiding post 111 of the present disclosure may be formed by a plurality of needle filaments 113 having flat ends and/or a plurality of small posts 114. The plurality of needle filaments 113 having the flat ends and the plurality of small posts 114 are arranged adjacent to each other. Alternatively, the plurality of said needle filaments 113 having the flat ends are arranged adjacent to each other. Alternatively, the plurality of small posts 114 are arranged adjacent to each other. A gap between two adjacent needle filaments 113 having the flat ends serves as the channel 115 which serves as the capillary liquid storage unit 120. A gap between two adjacent small posts 114 serves as the channel 115 which serves as the capillary liquid storage unit 120. A gap between one needle filament 113 having the flat end and one small post 114 serves as the channel 115 which serves as the capillary liquid storage unit 120. The needle filament or the small post 114 in the present embodiment may be solid or hollow. The capillary may be formed by the gap, which is defined by splicing the needle filaments or the small posts 114. Alternatively, the needle filament or the small post 114 may be configured to be hollow to provide an auxiliary capillary.

In an embodiment, the channel (115) extends vertically or spirally from the first end face (1111) towards the second end face (1112). An end of the channel (115) may extend through or approach the second end face (1112). The channel (115) may extend vertically along the liquid guiding post (111) to reach the first end face (1111). The channel (115) may be an annular groove defined in the outer wall of the liquid guiding post (111), and a plurality of annular grooves are spaced apart from each other and are defined in the outer wall of the liquid guiding post (111).

Embodiment 6

Figure 1D:
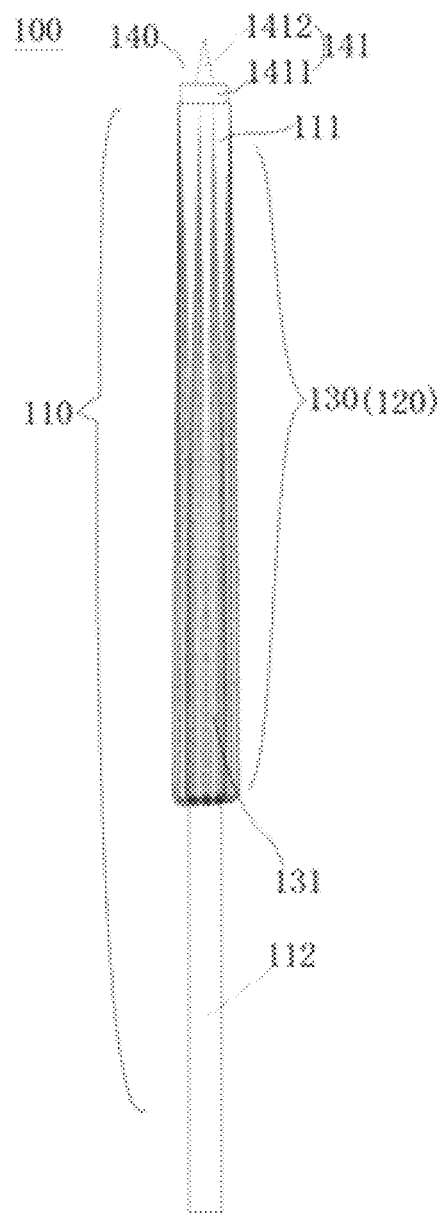
FIG. 1(d) is another structural schematic view of an introduction needle according to an embodiment of the present disclosure.

As shown in FIG. 1(d), the capillary liquid storage unit 120 in the present disclosure may be arranged by attaching a structure to an outside of the liquid guiding post. In the present embodiment, a liquid storage structure 130 is provided and includes one or more sheets. The sheets are attached to the outer wall of the liquid guiding post 111, and a gap is defined between the outer wall of the liquid guiding post 111 and the sheets. The gap serves as the capillary liquid storage unit 120. The capillary liquid storage unit 120 stores liquid temporarily. The liquid is guided to flow to the needle tooth 1412 of the needle piercing portion 140.

In an embodiment, the liquid storage structure 130 is formed by natural or man-made porous sheets.

In another embodiment, the liquid storage structure 130 includes a plurality of filaments. The plurality of filaments include fiber filaments 131. A gap between the plurality of fiber filaments 131 and a gap between the fiber filaments 131 and the outer wall of the liquid guiding post 111 serve as the capillary liquid storage unit 120. The capillary liquid storage unit 120 stores liquid temporarily. The liquid is guided to flow to the needle tooth 1412 of the needle piercing portion 140.

In an embodiment, the fiber filaments 131 may include animal hair, plant fiber filaments 131, chemical fiber filaments, and so on.

In an embodiment, the filaments may further include metal filaments. A gap between a plurality of metal filaments and a gap between the metal filaments and the outer wall of the liquid guiding member 110 serve as the capillary storage unit 120. The capillary storage unit 120 stores liquid temporarily, and the liquid is guided to flow to the needle tooth 1412 of the needle piercing portion 140.

In an embodiment, a position to which the liquid storage structure 130 is attached and area that the attached liquid storage structure 130 occupies may be determined based on a unit amount of ink stored in the liquid storage structure 130 and a target amount of stored ink of the liquid guiding member 110. Alternatively, the number of layers of the liquid storage structure 130 and the area of the liquid storage structure 130 may be determined based on the amount of ink used for tattoo.

Embodiment 7

The introduction needle provided in the present disclosure, serving as a tattoo tool, may introduce the tattoo ink 300 into the superficial layer of the skin. Therefore, a liquid guiding path may be formed between the ink 300 adsorbed into the liquid guiding member 110 and the needle tooth 1412 to ensure the ink 300 in the liquid guiding member 110 to flow to the tip of the needle tooth 1412 to be further introduced into the skin. Therefore, in the introduction needle of the present disclosure, one corner or one edge of at least one substrate 1411 of the piercing projection 141 needs to be disposed near the edge of the outer wall of the liquid guiding member 110. In this way, the needle tooth 1412 arranged on the substrate 1411 may receive the liquid flowing from the liquid guiding member 110. The above structure is necessary to effectively define the liquid guiding path to reduce the rate of empty needles. As shown in FIG. 4(b) and FIG. 4(d), the outer edge of the substrate 1411 of the piercing projection 141 has a portion that is substantially aligned with the outer edge of the liquid guiding post 111. The aligned portion ensures that the ink in the liquid guiding post 111 may flow to the tip of the needle tooth 1412. Similar structures are shown in FIG. 17(a) to FIG. 17(b) or FIG. 18(a) to FIG. 18(b).

In an embodiment, one corner or one edge of the substrate 1411 of the piercing projection 141 is substantially aligned with the edge of the outer wall of the liquid guiding member 110.

In another embodiment, the substrate 1411 of the piercing projection 141 is disposed at a middle of an end face of the liquid guiding member 110, and the corner or the edge of the substrate 1411 is no more than 0.18 mm away from the edge of the outer wall of the liquid guiding member 110.

Embodiment 8

Figure 8:
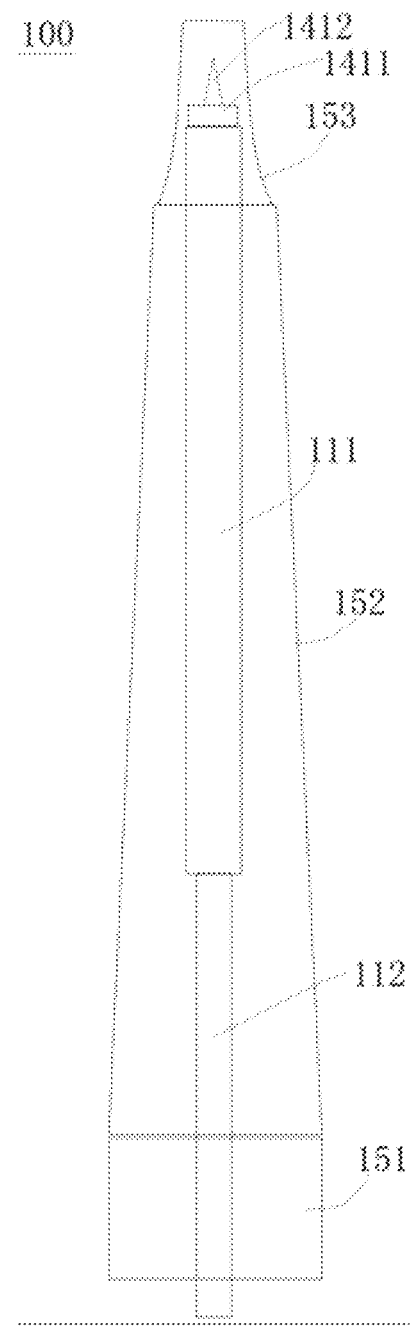
FIG. 8 is a schematic view of the introduction needle according to an embodiment of the present disclosure, wherein the introduction needle has a case.
Figure 9:
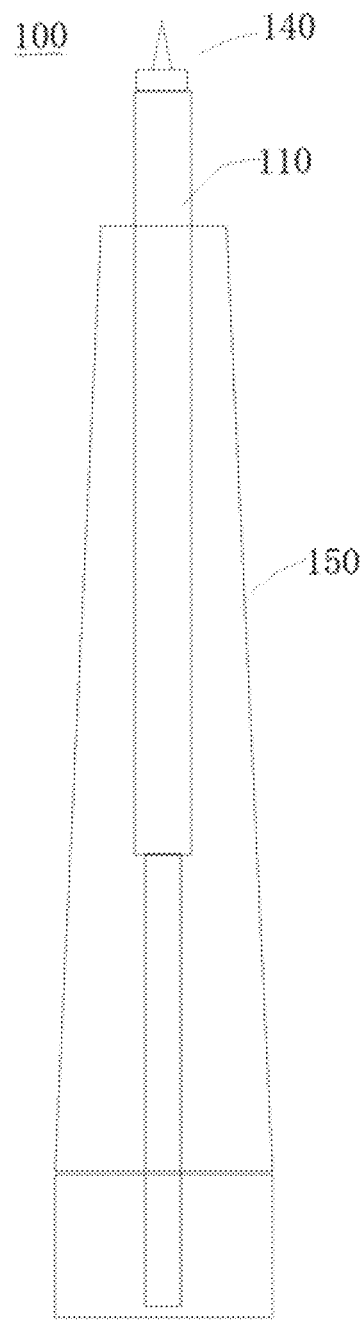
FIG. 9 is a schematic view of the structure shown in FIG. 8, wherein a needle outlet end of the case is omitted.
Figure 10:
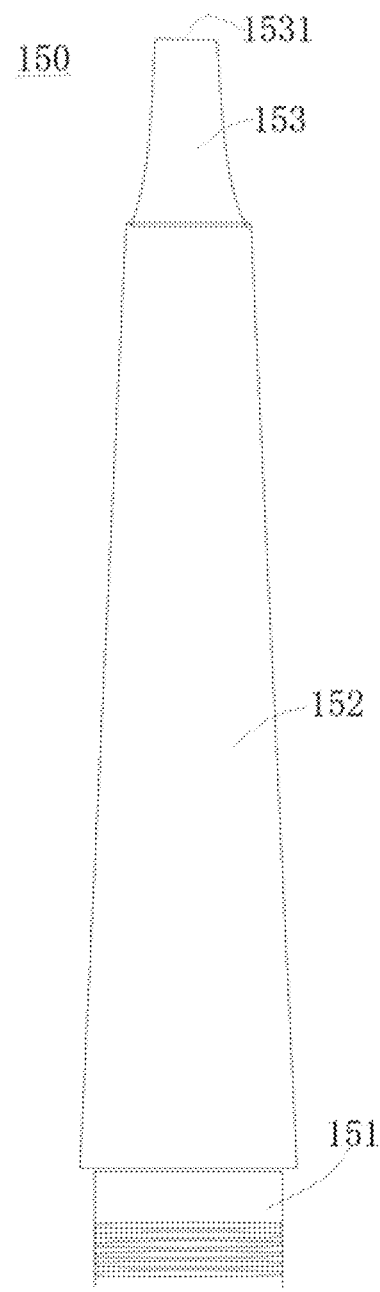
FIG. 10 is a schematic view of the case according to an embodiment of the present disclosure.

As shown in FIG. 8 to FIG. 10, the introduction needle of the present disclosure may further be arranged with a case 150. The liquid guiding member 110 is arranged inside the case 150. The liquid guiding member 110 may move reciprocately inside the case 150 to achieve the piercing operations.

In an embodiment, the case 150 of the present disclosure may be a tubular cylinder. As shown in FIG. 10, the case 150 may have a fastening end 151, an intermediate connecting tube 152, and a needle outlet end 153. The fastening end 151, the intermediate connecting tube 152, and the needle outlet end 153 are connected to each other sequentially to define a channel for the liquid guiding member 110 to move reciprocactely. Each of a central axis of the fastening end 151 and a central axis of the intermediate connecting tube 152 coincides with a central axis of the case 150.

In an embodiment, the fastening end 151 of the present disclosure is detachably connectable to an external drive member (such that the introduction needle may be replaced easily). The needle outlet end 153 defines a needle outlet port 1531. The needle tooth 1412 moves reciprocately at a location near the needle outlet port 1531. The liquid guiding member 110 and the needle piercing portion 140 disposed at an end of the liquid guiding member 110 are mounted, along the central axis of the case 150, in the intermediate connecting tube 152 of the case 150. The needle piercing portion 140 is disposed near the needle outlet end 153. The liquid guiding member 110 moves reciprocately in the intermediate connecting tube 152. Further, the liquid guiding member 110 drives the needle tooth 1412 of the needle piercing portion 140 to move out of the needle outlet port 1531 or to move to be retracted into needle outlet port 1531. It will be understood that the needle tooth 1412 may alternatively be slightly retracted and disposed outside of the needle outlet port 1531.

In an embodiment, the needle outlet end 153 of the case 150 of the present disclosure may be tubular.

The needle outlet port 1531 may have a flat port or a sloped port.

In the case that the needle outlet port 1531 is the flat port, when the liquid guiding member 110 moves freely and reciprocately at the needle outlet port 1531 of the needle outlet end 153 of the case 150, a gap between the outer wall of the liquid guiding member 110 and an inner wall of the needle outlet end 153 serves as a combined capillary space. Liquid may be temporarily stored in the combined capillary space when the needle is intaking the liquid. The liquid temporarily stored in the combined capillary may be guided by the gravitational force to flow to the needle piercing portion 140 and may be introduced into the surface layer 200 of the skin while the needle tooth 1412 of the needle piercing portion 140 is piercing into the skin.

In the case that the needle outlet port 1531 is the sloped port, when the liquid guiding member 110 is moving freely and reciprocately at the needle outlet port 1531 at the needle outlet end 153 of the case 150, a gap between the outer wall of the liquid guiding member 110 and an inner wall of the sloped port serves as a combined capillary space. Liquid is temporarily stored in the combined capillary space when the needle is intaking the liquid. The liquid temporarily stored in the combined capillary space is guided to flow to the needle piercing portion 140 and is introduced into the surface layer of the skin while the needle tooth 1412 of the needle piercing portion 140 is piercing the skin. The outer wall of the liquid guiding member 110 may abut against the inner wall of the sloped port. In this case, the sloped port serves as a limiting plate for the liquid guiding post, allowing the liquid guiding post to be vertically piercing into the skin surface layer. In an embodiment, an angle may be formed between the central axis of the case and a plane in which the plate of the sloped port is located. When the liquid guiding member is moving, the sloped port may provide abutting for the liquid guiding member.

Embodiment 9

While performing tattoo, the introduction needle is operating at a relatively high frequency. Therefore, while the needle is piercing the skin, the needle may be deviated and skewed, resulting in needle slippage. Therefore, the present disclosure provides an introduction needle to limit the liquid guiding member 110, assisting the liquid guiding member 110 to pierce into and leave out of the skin in a straight direction, and the piercing may be accurately performed.

As shown in FIG. 12(a) to FIG. 12(d), FIG. 11(a), and FIG. 11(b), a limiting structure 160 is arranged inside the case 150 of the introduction needle in the present embodiment. The limiting structure 160 is disposed inside the intermediate connecting tube 152 of the case 150 and/or on the fastening end 151 of the case 150 and/or on the needle outlet end 153 of the case 150. When the liquid guiding member 110 is moving reciprocately along the central axis of the case 150, the liquid guiding member 110 may abut against the limiting structure 160. The limiting structure 160 limits the liquid guiding member 110 from swinging in a direction along a cross section of the case 150. In this way, the liquid guiding member 110 drives the needle tooth 1412 of the needle piercing portion 140 to vertically move out of the case 150 to pierce into the skin surface 200. Further, the liquid guiding member 110 drives the needle tooth 1412 of the needle piercing portion 140 to vertically move from the outside of the needle outlet port 1531 to the inside of the case 150. It will be understood that the needle tooth 1412 may alternatively be slightly retracted and still located outside the case 150.

Figure 11A:
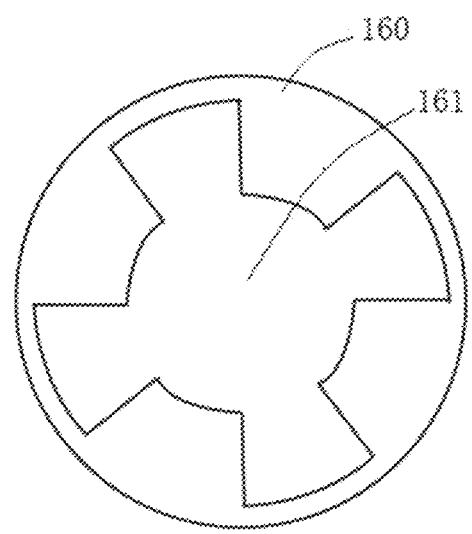
FIG. 11(a) is a cross-sectional view of a limiting structure according to an embodiment of the present disclosure, wherein the limiting structure is a knurled limiting hole.
Figure 11B:
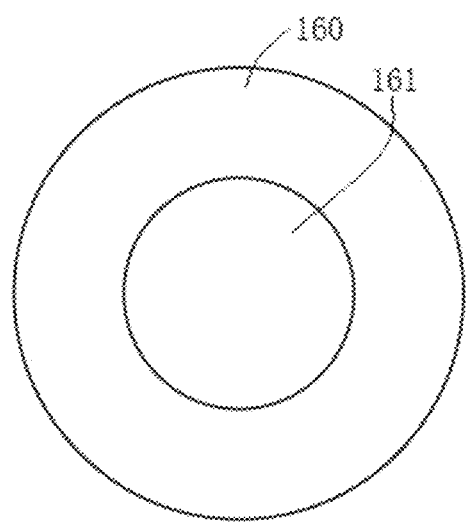
FIG. 11(b) is a cross-sectional view of a limiting structure according to another embodiment of the present disclosure, wherein the limiting structure is a circular limiting hole.

In an embodiment, the limiting structure 160 of the present disclosure may be a limiting hole 161. The limiting hole 161 may be a through hole. A central axis of the through hole may or may not coincide with the central axis of the liquid guiding member 110. Preferably, the central axis of the through hole does not coincide with the central axis of the liquid guiding member 110. An inner diameter of the through hole may be adapted to an outer diameter of the liquid guiding member 110. For example, a shape and a size of the central through hole may be adapted to a shape and a size of the largest cross section of the liquid guiding member 110. The adaptation in this case may not refer to the shape and the size of the through hole being identical to the shape and the size of the largest cross section of the liquid guiding member, but allows the liquid guiding member to pass through the through hole. In an embodiment, a cylindrical liquid guiding member may be adapted with a square through hole. In this case, a gap between the cylindrical liquid guiding member and the square through hole may provide the capillary effect to store the liquid, ensuring the liquid guiding member 110 to move straight in the central through hole (the limiting structure provides abutting to the liquid guiding member to limit the liquid guiding member from swinging in a lateral direction and to ensure the liquid guiding member to move straight in central through hole). In this way, the central through hole limits a position of the liquid guiding member 110. The central through hole may be circular or irregularly shaped. As shown in FIG. 11(a), when the through hole is irregularly shaped, the through hole may be suitable for various shapes of liquid guiding members.

In an embodiment, the limiting structure 160 of the present disclosure may be a limiting tube 162. The limiting tube 162 has a channel. A central axis of the channel may or may not coincide with the central axis of the liquid guiding member 110. An inner diameter of the channel is adapted to the outer diameter of the liquid guiding member 110. A shape and a size of the channel are adapted to the shape and the size of the largest cross section of the liquid guiding member 110. The adaptation in this case may not refer to the shape and the size of the channel being identical to the shape and the size of the largest cross section of the liquid guiding member, but allows the liquid guiding member to pass through the channel. In an embodiment, the cylindrical liquid guiding member may be adapted with a square channel. In this case, a gap between the cylindrical liquid guiding member and the square channel may provide the capillary effect to store the liquid, ensuring the liquid guiding member 110 to move straight in the central channel. The central channel limits the position of the liquid guiding member 110.

Figure 12A:
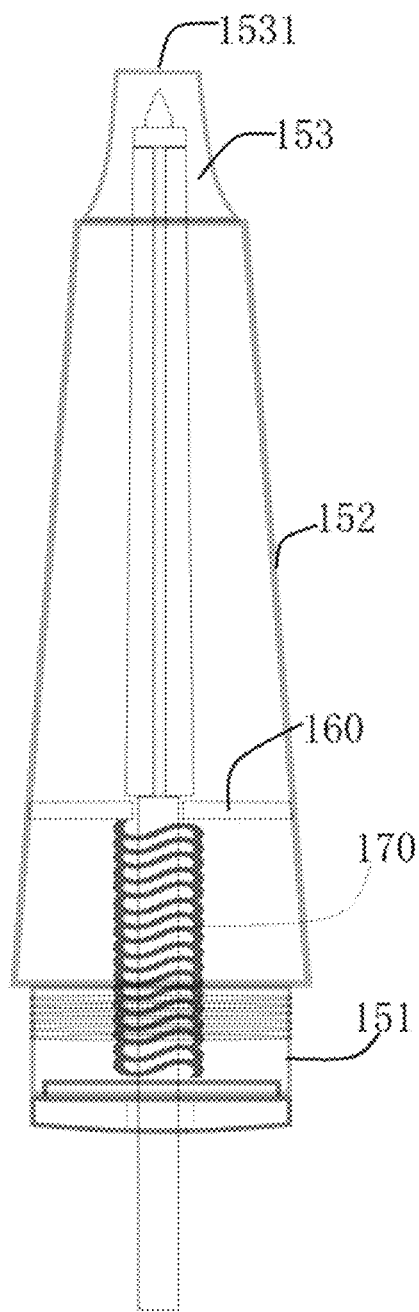
FIG. 12(a) is a structural schematic view of the introduction needle according to an embodiment of the present disclosure.
Figure 12B:
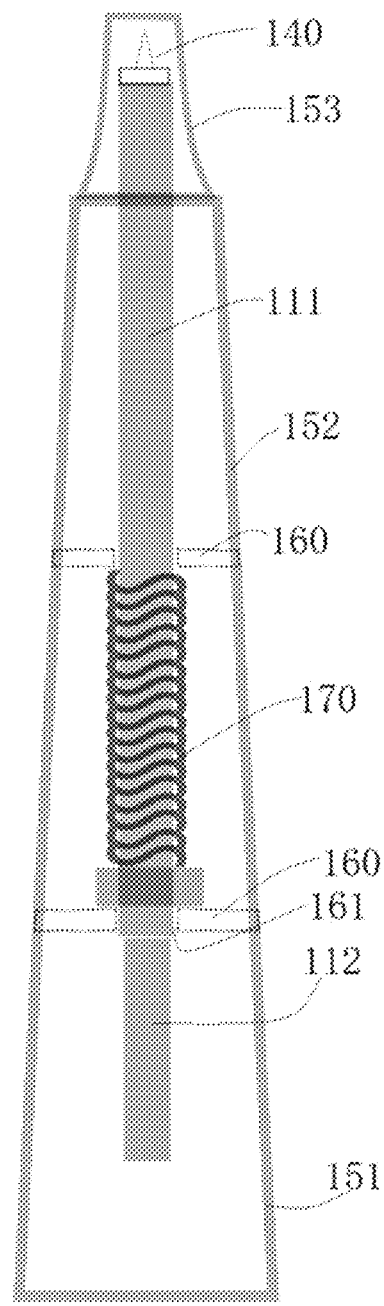
FIG. 12(b) is another structural schematic view of the introduction needle according to an embodiment of the present disclosure.
Figure 12C:
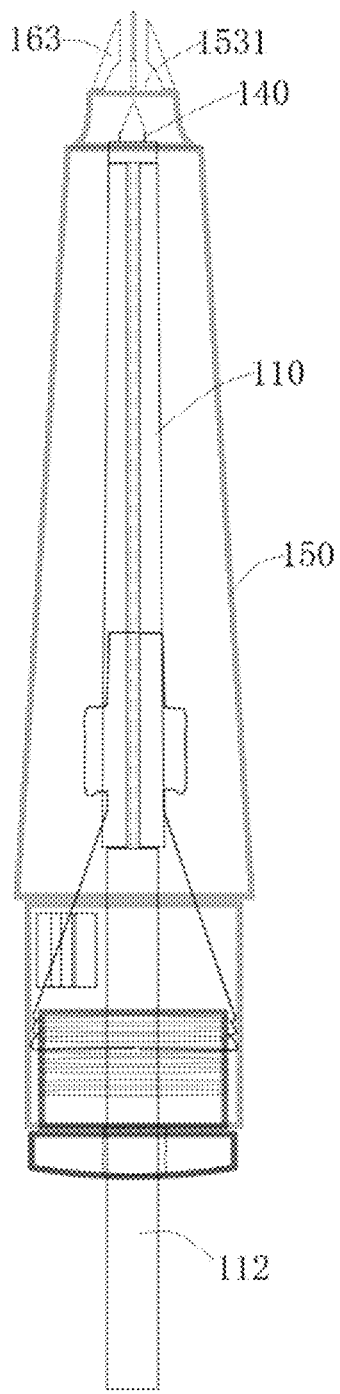
FIG. 12(c) is another structural schematic view of the introduction needle according to an embodiment of the present disclosure.
Figure 12D:
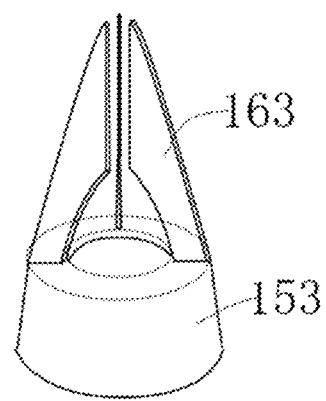
FIG. 12(d) is a perspective view of a needle outlet end of the introduction needle shown in FIG. 12(c).
Figure 12E:
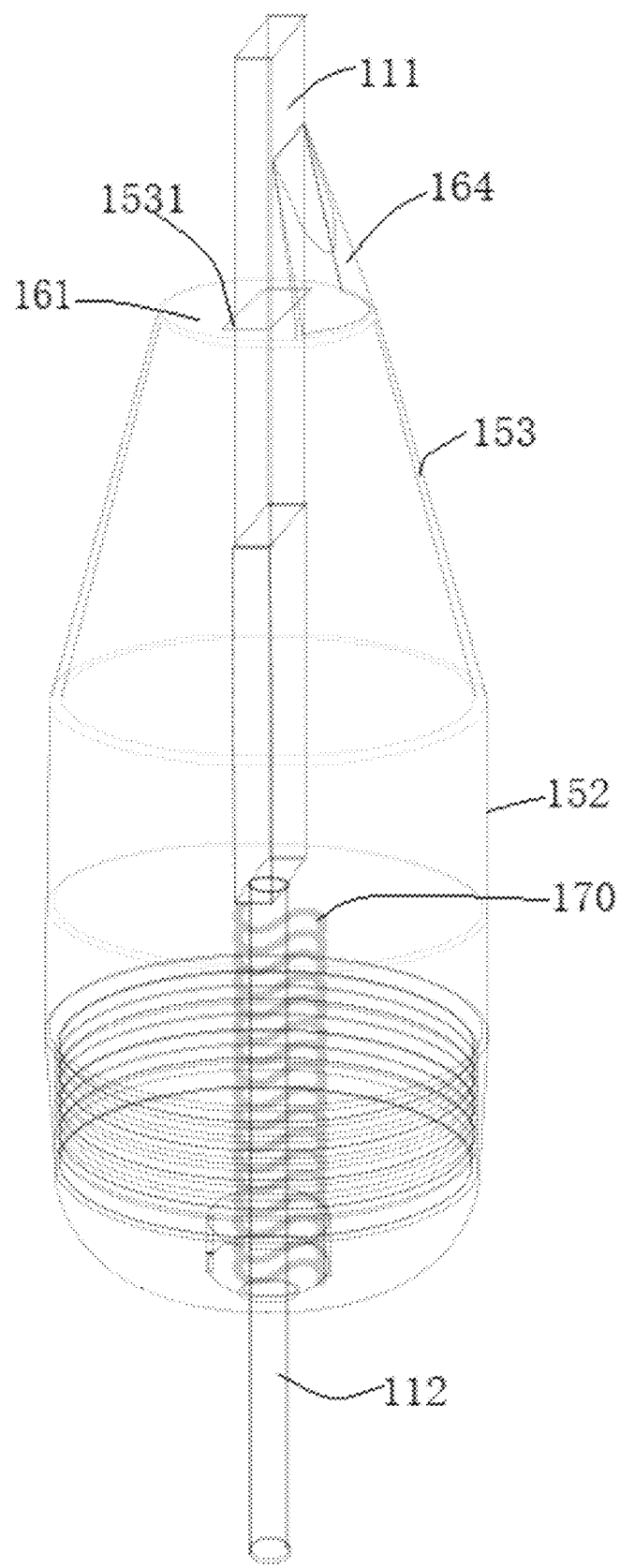
FIG. 12(e) is a structural schematic view of the introduction needle according to an embodiment of the present disclosure.
Figure 13A:
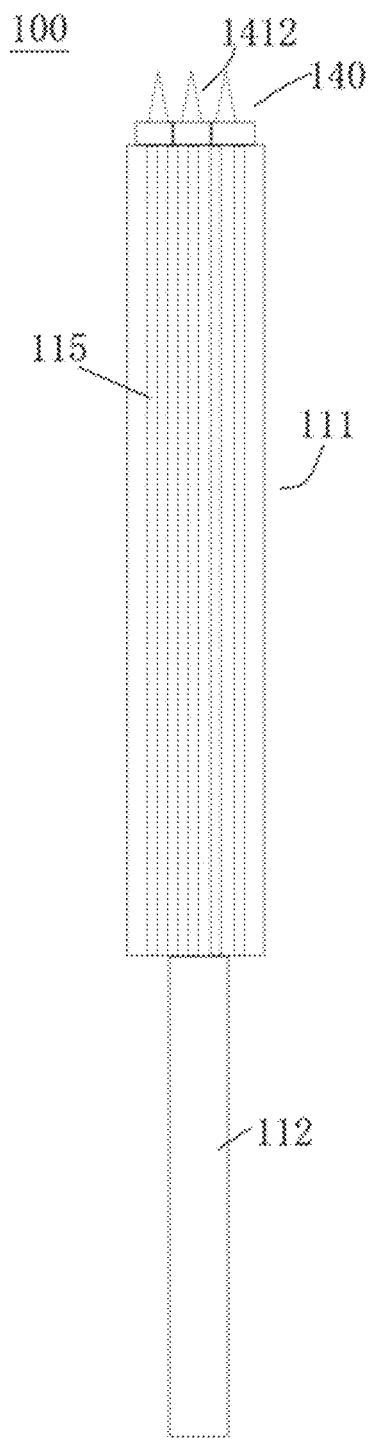
FIG. 13(a) is a structural schematic view of the introduction needle according to an embodiment of the present disclosure.
Figure 13B:
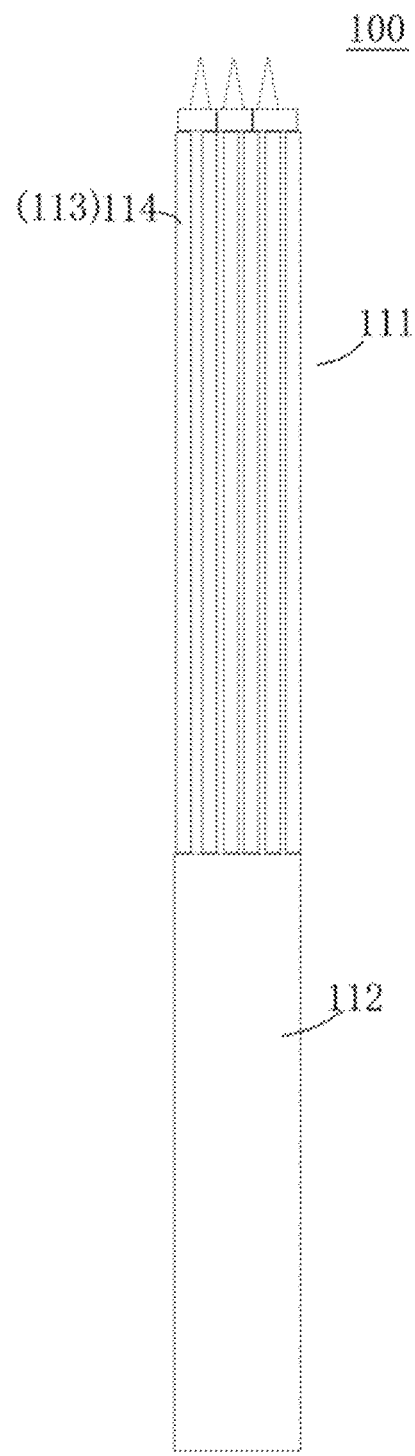
FIG. 13(b) is another structural schematic view of the introduction needle according to an embodiment of the present disclosure.
Figure 13C:
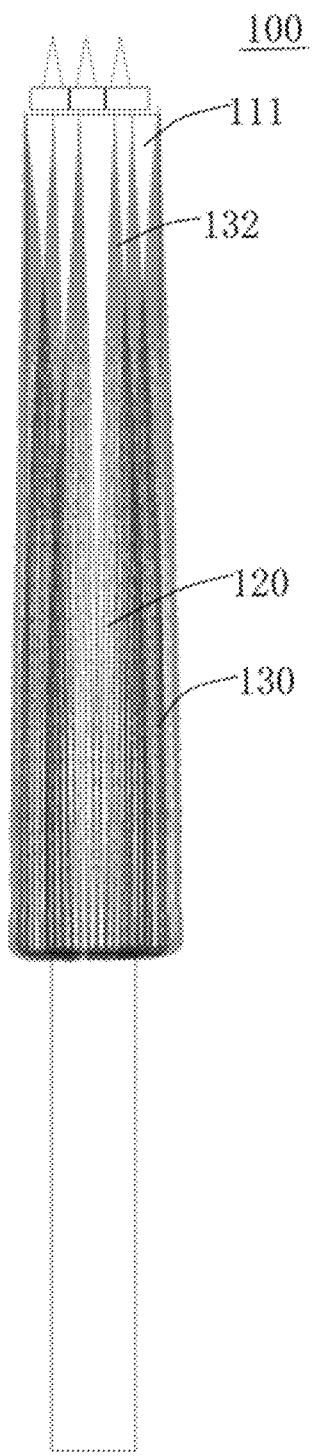
FIG. 13(c) is another structural schematic view of the introduction needle according to an embodiment of the present disclosure.
Figure 14A:
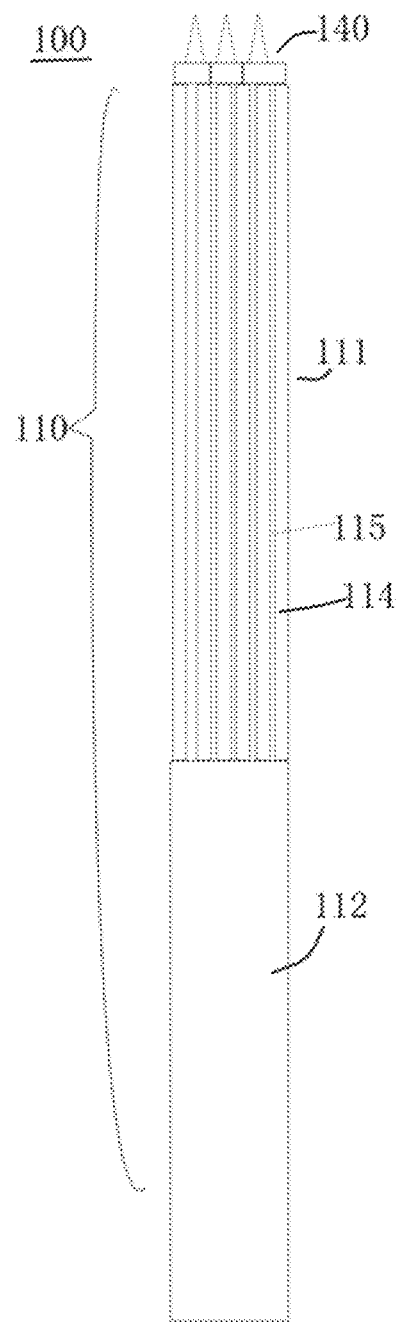
FIG. 14(a) is a structural schematic diagram of the introduction needle according to another embodiment of the present disclosure.
Figure 14B:
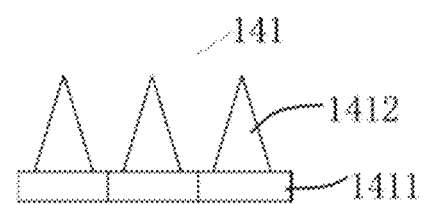
FIG. 14(b) is a planar schematic diagram of a piercing projection of a needle piercing portion according to an embodiment of the present disclosure.
Figure 14C:
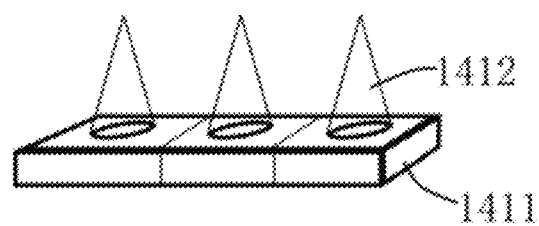
FIG. 14(c) is a perspective view of the piercing projection shown in FIG. 14(b).
Figure 15A:
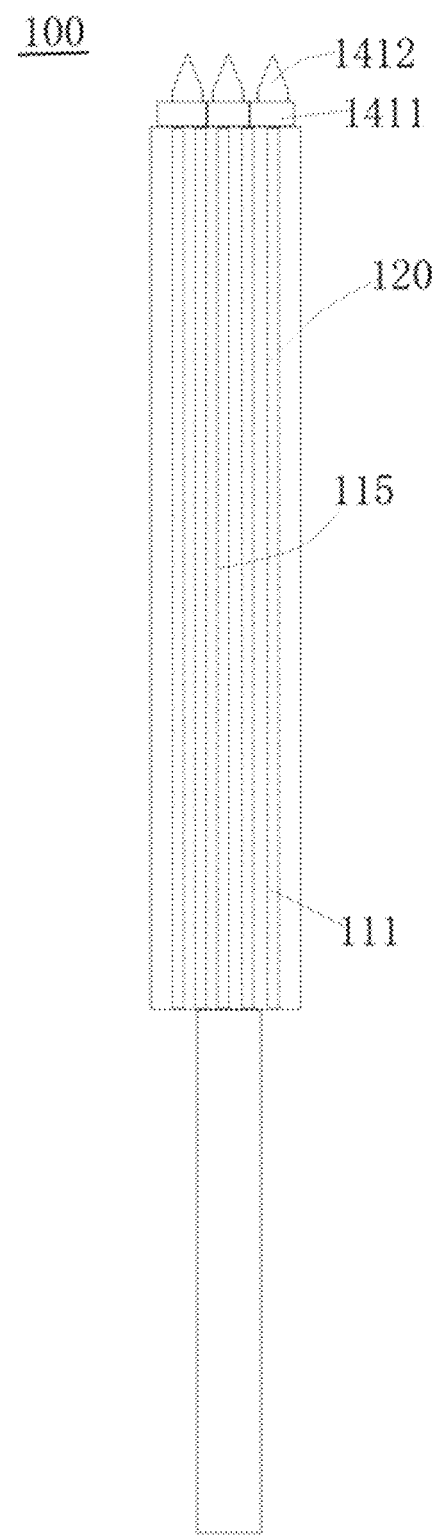
FIG. 15(a) is a structural schematic view of an introduction needle according to still another embodiment of the present disclosure.
Figure 15B:
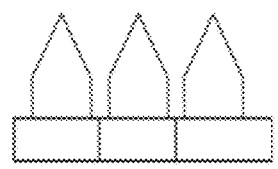
FIG. 15(b) is a planar schematic diagram of a piercing projection of a needle piercing portion according to an embodiment of the present disclosure.
Figure 15C:
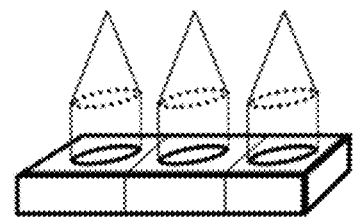
FIG. 15(c) is a perspective view of the piercing projection shown in FIG. 15(b).
Figure 16:
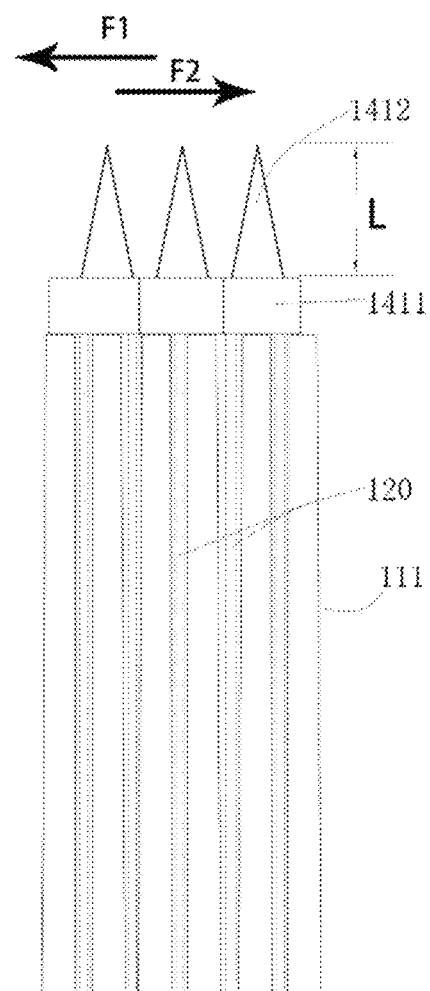
FIG. 16 is a structural schematic view of a liquid guiding post and a piercing projection according to an embodiment of the present disclosure.
Figure 17A:
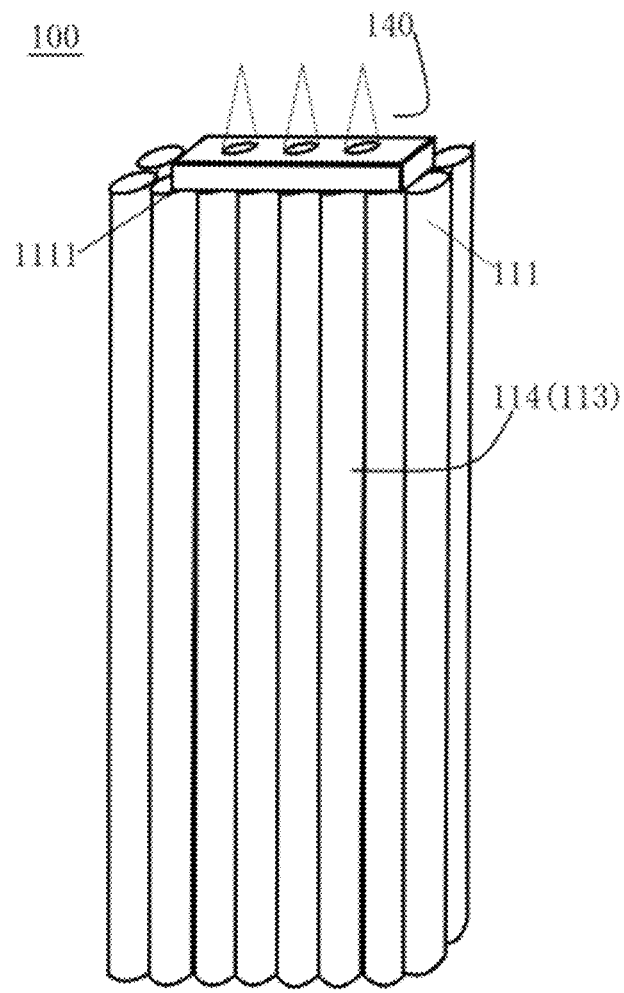
FIG. 17(a) is a perspective view of a portion of the introduction needle described according to an embodiment of the present disclosure.
Figure 17B:
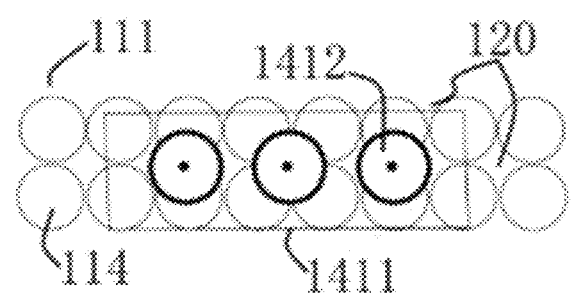
FIG. 17(b) is a planar schematic view of the introduction needle shown in FIG. 17(a), viewed from a viewing angle.
Figure 18A:
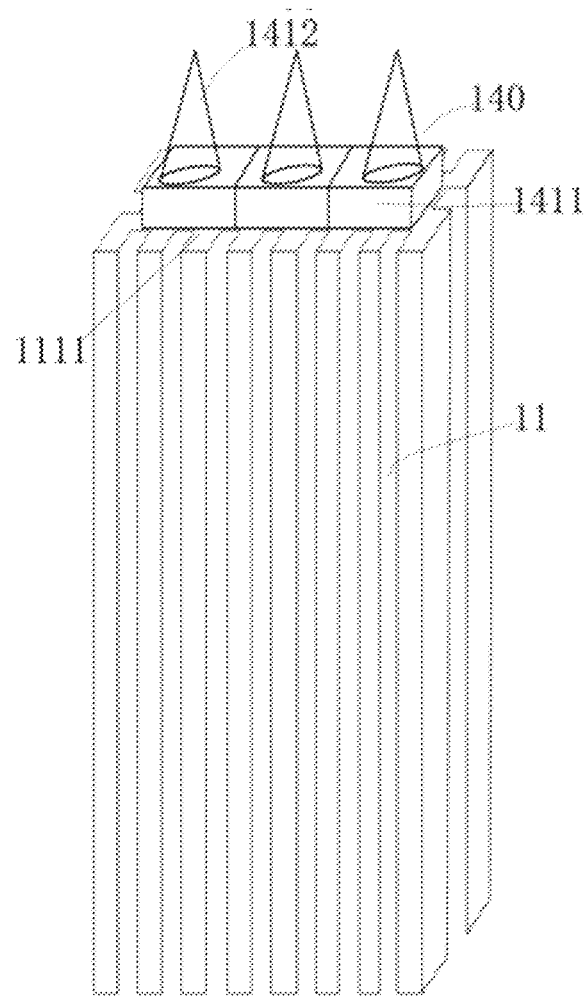
FIG. 18(a) is a perspective view of a portion of the introduction needle according to another embodiment of the present disclosure.
Figure 18B:
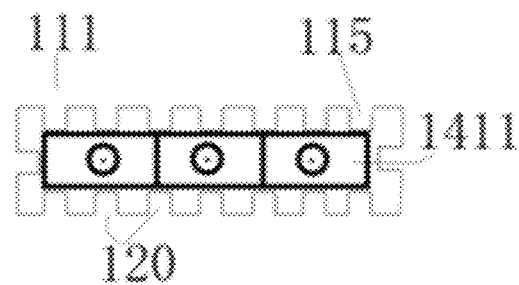
FIG. 18(b) is a planar schematic view of the introduction needle shown in FIG. 18(a), viewed from a viewing angle.

In an embodiment, as shown in FIG. 12(e), the limiting structure 160 of the present disclosure may be a limiting plate 164. The limiting plate 164 has a limiting surface. An angle is generated between a plane in which the limiting surface is located and the central axis of the liquid guiding member 110. In one case, the plane in which the limiting surface is located may be parallel to the central axis of the liquid guiding member 110. When the liquid guiding member 110 is moving reciprocately along the central axis of the case 150, the liquid guiding member 110 abuts against the limiting surface. The limiting surface limits the liquid guiding member 110 from swinging in the direction of the cross section of the case 150. The limiting plate 164 of the present disclosure may be disposed at the needle outlet port 1531 of the needle outlet end 153 of the case 150. One or more limiting structures 164 may be arranged. When more than one limiting structures 164 are arranged, the more than one limiting structures 164 may be evenly distributed at the needle outlet port 1531 to define a channel, and the needle piercing portion 140 may move straight in and out of the channel.

As shown in FIG. 12(c) and FIG. 12(d), in an embodiment, the limiting structure 160 of the present disclosure may be a limiting bracket 163. The limiting bracket 163 is disposed at an end of the case 150 (or disposed inside the case). The limiting bracket 163 includes one or more sub-brackets. For each of the one or more sub-brackets, a side of the sub-bracket abuts against the liquid guiding member 110. The sub-brackets limit the liquid guiding member 110 from swinging in the direction of the cross section of the case 150. When the liquid guiding member 110 moves reciprocately along the central axis of the case 150, the liquid guiding member 110 abuts against a side of the sub-bracket. Further, due to abutting against the side of the sub-bracket, the liquid guiding member 110 is guided to move to the needle outlet port 1531 of the case 150.

The limiting structure 160 in the present embodiment may effectively limit and guide the liquid guiding member 110, ensuring the needle to pierce the skin at desired position accurately and preventing the needle from being skewed or from slipping.

Embodiment 10

As shown in FIG. 12(a) to FIG. 12(c), the introduction needle 100 in the present embodiment may further include an elastic member 170, such as a spring, a silicone member, or a rubber band. An end of the elastic member 170 is connected to the case 150, and the other end of the elastic member 170 is connected to the connecting rod of the liquid guiding member 110. The elastic member may be connected to the case or the liquid guiding member in various ways, such as connection by abutting, encased connection, or connection by hooks, and so on. The case 150 is connected to the motorized rod. When the liquid guiding member 110 is driven by an external force (a motor of the motorized rod is activated to apply a driving force to the liquid guiding member 110) to move along the central axis of the case 150 towards the needle outlet port 1531 of the case 150, the elastic member 170 is elastically deformed to drive the liquid guiding member 110 to move back to its initial position.

Embodiment 11

Different tattoo patterns and tattoo locations may require different tattoo needles to be used. The present disclosure further provides an introduction needle 100, and the piercing projection 141 of the introduction needle includes one or more substrates 1411. One needle tooth 1412 is arranged on each of the one or more substrates 1411. The one or more substrates 1411 are arranged into one row, and therefore, the corresponding needle teeth 1412 arranged on the corresponding one or more substrates 1411 are also arranged into one row.

As shown in FIG. 13(a) to FIG. 13(c), FIG. 14(a) to FIG. 14(c), FIG. 15(a) to FIG. 15(c), and FIG. 16, for one introduction needle, more than one needle teeth are arranged in a row. This type of introduction needle may be configured to produce a tattoo having a relatively long linear pattern and a small transition arc. Compared to the introduction needle having a single needle tooth, the introduction needle having more than one needle teeth in the present embodiment may produce specific patterns more quickly. Of course, in order to produce a tattoo having dots or having large transition arcs between linear patterns, the introduction needle having the single needle tooth may be more advantageous.

Figure 19:
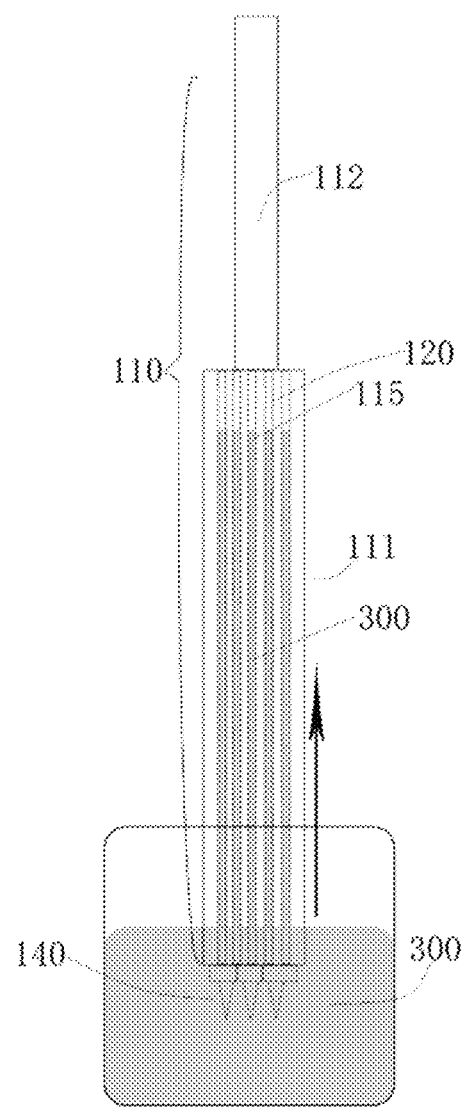
FIG. 19 is a schematic view showing a state of the introduction needle while the introduction needle is intaking ink, according to an embodiment of the present disclosure.
Figure 20:
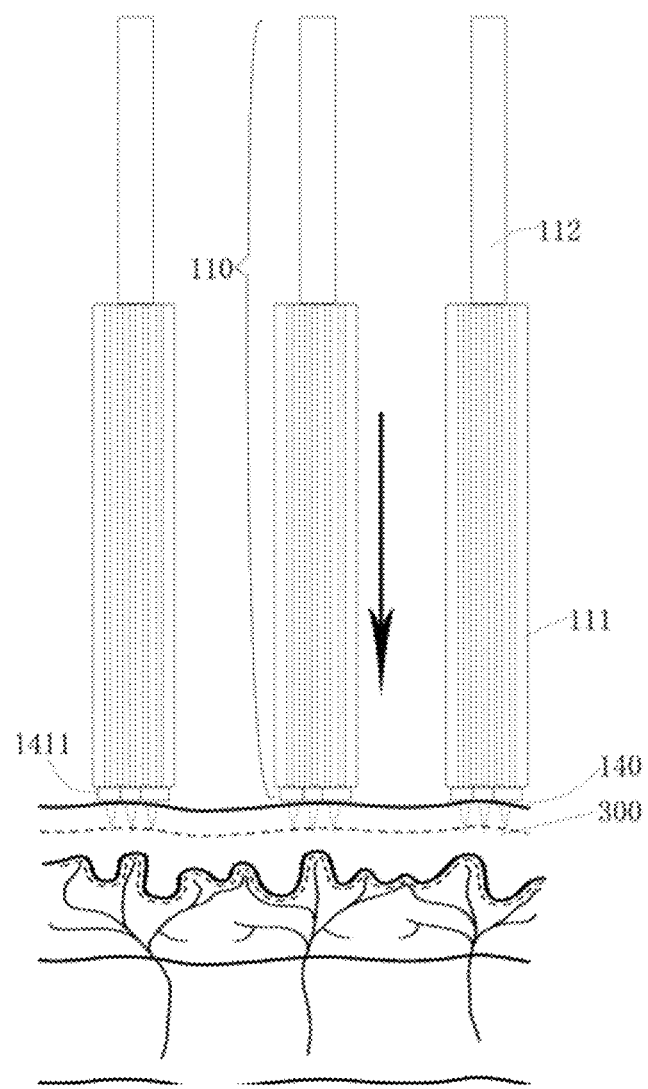
FIG. 20 is a schematic view showing a state of the introduction needle piercing into the skin, according to an embodiment of the present disclosure.

As shown in FIG. 19 and FIG. 20, FIG. 19 is a schematic view showing an in-use state of the introduction needle while intaking the ink. The needle piercing portion in the drawings has a plurality of substrates and a plurality of needle teeth. The ink in an ink bottle is adsorbed into the capillary liquid storage unit 120 from the end of the liquid guiding member. Further as shown in FIG. 20, when the introduction needle is being used to pierce into the skin, each of the plurality of substrates 1411 of the needle piercing portion 140 limits a depth that a corresponding one of the plurality of needle teeth 1412 pierces into the skin. As shown in the drawings, the plurality of needle teeth pierce into the skin at the same time. Such an arrangement of the substrates and the needle teeth allows the needle piercing portion to be more suitable for drawing lines.

Figure 21A:
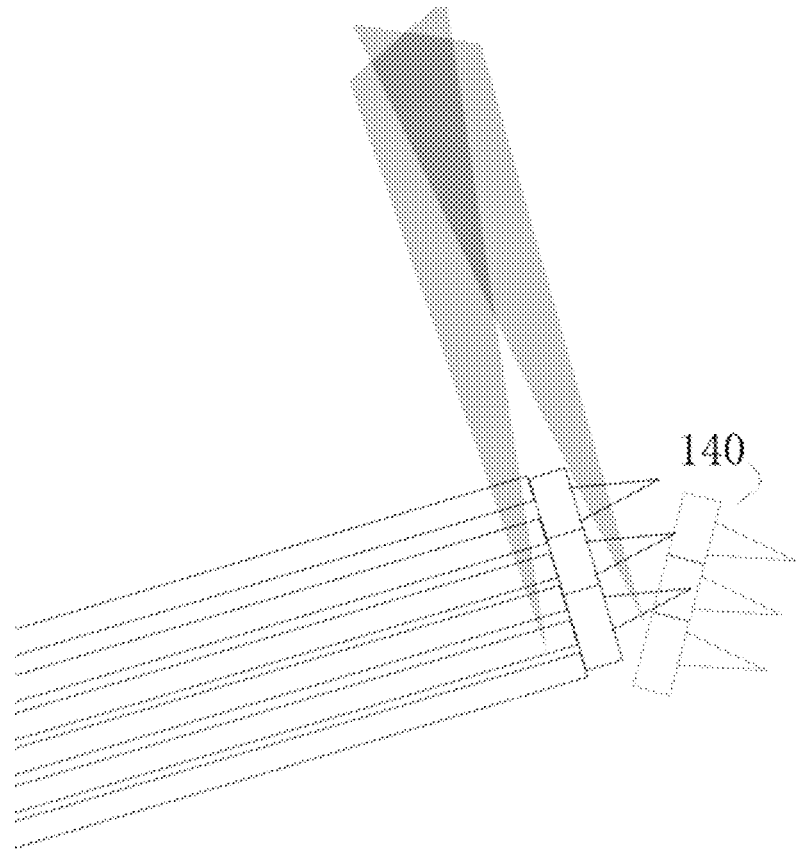
FIG. 21(a) is a schematic view showing a state of destroying an introduction needle after being used according to an embodiment of the present disclosure.
Figure 21B:
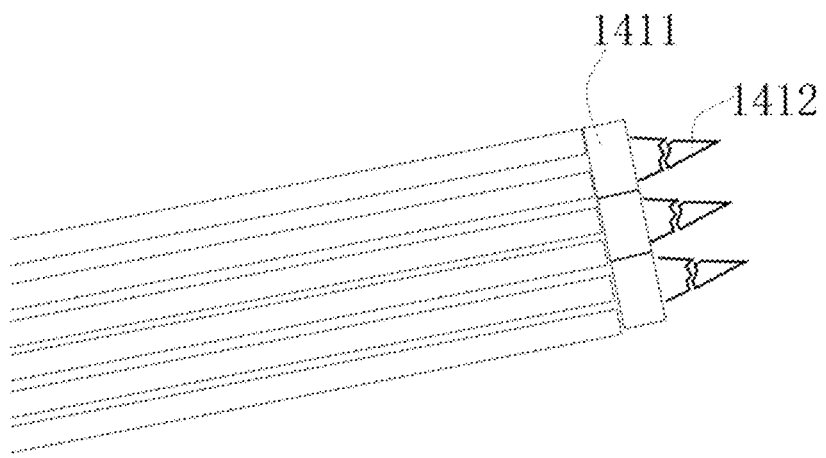
FIG. 21(b) is a schematic view showing a state of destroying an introduction needle after being used according to another embodiment of the present disclosure.

As shown in FIG. 21(a) and FIG. 21(b), the needle piercing portion having a single row of the plurality of needle teeth may also be destroyed simply.

Embodiment 12

Figure 25:
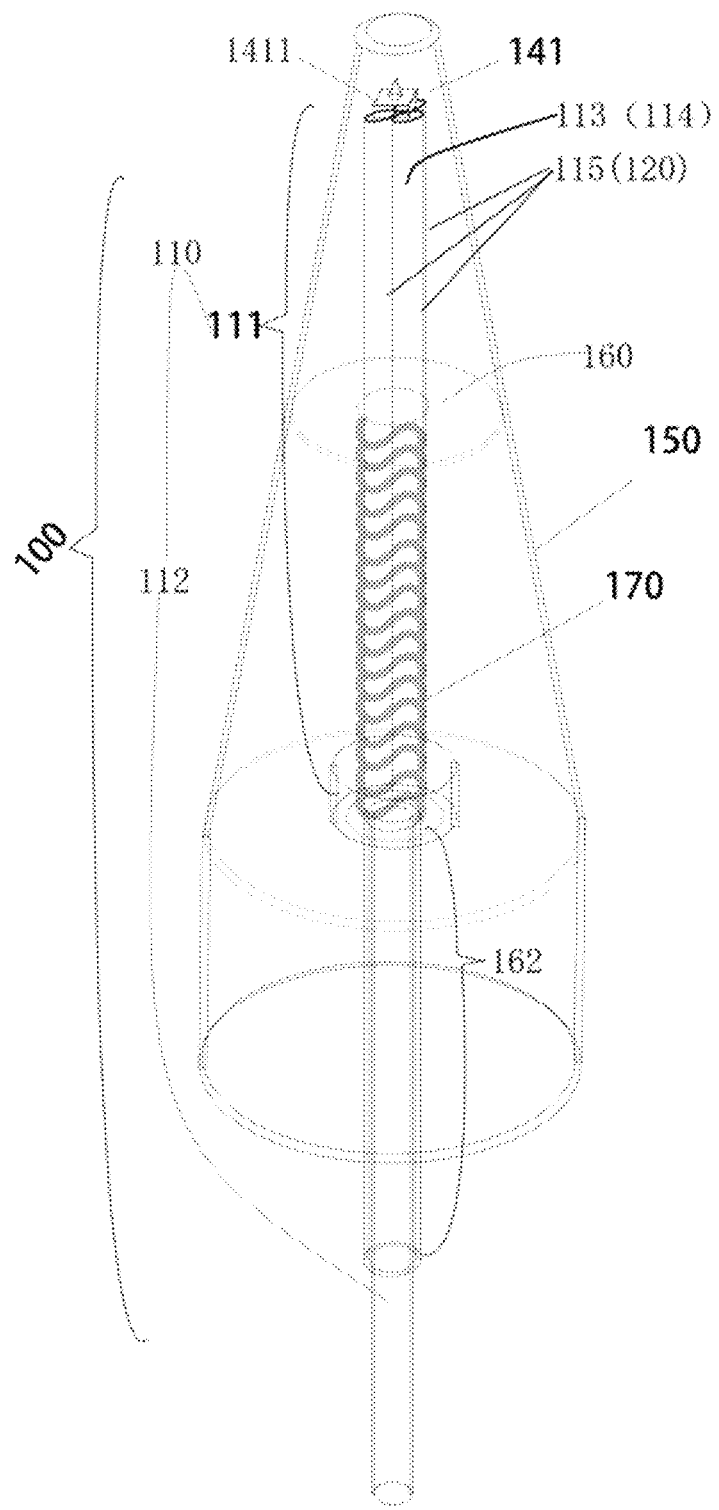
FIG. 25 is a structural schematic view of the introduction needle according to an embodiment of the present disclosure.

Based on the introduction needle of the present embodiment, the present disclosure further provides a tattoo device. As shown in FIG. 25, the tattoo device includes any one of the above-mentioned introduction needles 100 and an external drive member that drives the liquid guiding member 110 of the introduction needle 100 to move.

In an embodiment, the external drive member includes a manual rod, a motorized rod, and an intelligent arm.

In the description of the present disclosure, the terms "an embodiment", "some embodiments", "examples", "specific examples", or "some examples" mean that specific features, structures, materials or characteristics described in one embodiment or one example are included in at least one embodiments or examples of the present disclosure. In the present specification, exemplary expressions of the above terms may not be directed to the same embodiment or the same example. Moreover, the specific features, structures, materials, or characteristics described may be combined in any one or more embodiments or examples in a suitable manner. In addition, any ordinary skilled person in the art may join and combine different embodiments or examples described in the present specification.

Although embodiments of the present disclosure have been shown and described above, it is to be understood that the above embodiments are exemplary and are not to be interpreted as a limitation of the present disclosure. Any ordinary skilled person in the art may perform changes, modifications and variations on the above embodiments within the scope of the present disclosure.

What is claimed is:

1. An introduction needle, comprising a needle piercing portion and a liquid guiding member, wherein the needle piercing portion comprises a piercing projection, the piercing projection comprises a substrate and a needle tooth, the needle tooth is fixedly arranged on a side surface of the substrate, a central axis of the needle tooth is perpendicular to the side surface of the substrate; and wherein the piercing projection is disposed at an end of the liquid guiding member, the liquid guiding member is columnar, a side surface of the other side of the substrate is fixed to the end of the columnar liquid guiding member, a central axis of the columnar liquid guiding member is parallel to the central axis of the needle tooth.

2. The introduction needle according to claim 1, wherein the liquid guiding member comprises a liquid guiding post and a connecting rod connected to the liquid guiding post, the connecting rod is connected to a drive portion, the liquid guiding member is driven by the drive portion to move reciprocately along the central axis of the liquid guiding member; and the liquid guiding post has a first end face and a second end face, a central axis of the liquid guiding post extends through a center of the first end face and a center of the second end face, and the side surface of the other side of the substrate is fixed to the first end face of the liquid guiding post.

3. The introduction needle according to claim 2, wherein an axial length of the liquid guiding post is greater than a length of a longer edge of a cross section of the first end face of the liquid guiding post or greater than a diameter of the first end face; and the axial length of the liquid guiding post is at least two times of a length of the shortest edge of the first end face of the liquid guiding post or at least two times of the diameter of the first end face, and the axial length of the liquid guiding post is greater than the length of the longest edge of the first end face or greater than the diameter of the first end face.

4. The introduction needle according to claim 1, wherein the needle tooth is a protrusion protruding from the substrate, a size of a cross sectional area of the protrusion decreases in a direction from the substrate towards a free end of the protrusion, a bottom face of the needle tooth is connected to the substrate, the free end of the needle tooth is a top end of the protrusion, a height of the needle tooth is in a range from 50 μm to 1500 μm, and a diameter of the bottom face of the needle tooth is in a range from 50 μm to twice the height of the needle tooth.

5. The introduction needle according to claim 1, wherein the needle tooth comprises a tail pin and a top pin, the top pin and an end of the tail pin are configured as a one-piece and integral structure, the tail pin is columnar, the top pin is protruding from the tail pin, a size of a cross sectional area of the top pin decreases in a direction extending from the tail pin to a free end of the top pin away from the tail pin, the other end of the tail pin is fixedly connected to the substrate.

6. The introduction needle according to claim 1, wherein the liquid guiding post is arranged with a capillary liquid storage unit configured to store liquid, the liquid guiding post is configured to guide the liquid to flow to the needle piercing portion; and
    the needle tooth is configured to pierce into a surface layer of skin, and the liquid is capable of being introduced, along the needle tooth, into the surface layer of the skin.

7. The introduction needle according to claim 6, wherein the liquid guiding post defines a plurality of channels, the plurality of channels are defined in an outer wall of the liquid guiding post and/or in an interior of the liquid guiding post, the plurality of channels cooperatively serves as the capillary liquid storage unit; and
    when at least one of the plurality of channels stores liquid, the liquid in the at least one of the plurality of channels is capable of being guided to flow to the needle tooth.

8. The introduction needle according to claim 7, wherein each of the plurality of channels extends from the first end face towards the second end face.

9. The introduction needle according to claim 7, wherein the liquid guiding post comprises a plurality of small sub-posts arranged adjacent to each other, a gap defined between adjacent two of the plurality of small sub-posts serves as any of the plurality of channels serving as the capillary liquid storage unit.

10. The introduction needle according to claim 6, wherein the liquid guiding post is arranged with a liquid storage structure on the outer wall of the liquid guiding post, the liquid storage structure comprises one or more porous sheets, the one or more porous sheets are attached to the outer wall of the liquid guiding post, a gap is defined between the one or more porous sheets and the outer wall of the liquid guiding post; and
    when liquid is stored in the capillary storage unit, the liquid is capable of being guided to flow to the needle tooth of the needle piercing portion.

11. The introduction needle according to claim 6, wherein the liquid guiding post is arranged with a liquid storage structure on the outer wall of the liquid guiding post, the liquid storage structure comprises a plurality of filaments, each of the plurality of filaments comprises a fiber filaments, a gap between a plurality of fiber filaments and a gap between the plurality of fiber filaments and the outer wall of the liquid guiding post serve as the capillary liquid storage unit; and
    when liquid is stored in the capillary storage unit, the liquid is capable of being guided to flow to the needle tooth.

12. The introduction needle according to claim 1, wherein one corner or one edge of the substrate is disposed in proximity to or aligned with an edge of the outer wall of the liquid guiding member, allowing the needle tooth disposed on the substrate to receive liquid flowing from the liquid guiding member.

13. The introduction needle according to claim 12, wherein the substrate is disposed at a middle of an end face of the liquid guiding member, and a distance from the one corner or the one edge of the substrate to the edge of the outer wall of the liquid guiding member is not greater than 0.18 mm.

14. The introduction needle according to claim 1, further comprising a case,
    wherein the case is a tubular cylinder, the case has a fastening end, an intermediate connecting tube, and a needle outlet end; the fastening end, the intermediate connecting tube and the needle outlet end are connected with each other in sequence to form a channel in which the liquid guiding member is configured to move reciprocately; each of a central axis of the fastening end and a central axis of the intermediate connecting tube coincides with a central axis of the case;
    the fastening end is detachably connected to an external drive member, the needle outlet end defines a needle outlet port; and
    the liquid guiding member and the piercing projection are mounted in the intermediate connecting tube of the case along the central axis of the case, the piercing projection is disposed near the needle outlet end (153), the liquid guiding member is configured to move reciprocately in the intermediate connecting tube and is configured to drive the needle tooth to move to an outside or to retract the needle tooth to an inside of the needle outlet port.

15. The introduction needle according to claim 14, wherein the case is arranged with a limiting structure, the limiting structure is disposed inside the intermediate connecting tube of the case and/or on the fastening end of the case and/or at the needle outlet end of the case;
    when the liquid guiding member moves reciprocately along the central axis of the case, the liquid guiding member abuts against the limiting structure, and the limiting structure is configured to limit the liquid guiding member from swinging in a direction of a cross section of the case, and the liquid guiding member is configured to drive the needle tooth to move vertically out of the case to pierce into the surface of the skin and configured to retract the needle tooth vertically to the inside of the needle outlet port.

16. The introduction needle according to claim 15, wherein the limiting structure comprises a limiting hole, the limiting hole is a through hole;
    when the liquid guiding member is moving reciprocately along the central axis of the case, the liquid guiding member abuts against a wall of the through hole, and the wall of the through hole is configured to limit the liquid guiding member from swinging in the direction of the cross section of the case.

17. The introduction needle according to claim 14, wherein,
    the needle outlet end is tubular;
    the needle outlet port is a flat port or a sloped port;
    the liquid guiding member is freely retractable at the needle outlet port; when the liquid guiding member moves reciprocately within the case, a gap between the outer wall of the liquid guiding member and an inner wall of the needle outlet end serves as a combined capillary space; when the combined capillary space is intaking liquid, the liquid stored in the combined capillary space is capable of being guided to flow to the needle piercing portion and is capable of being introduced into the surface layer of the skin while the needle tooth of the needle piercing portion pierces into the skin.

18. The introduction needle according to claim 14, further comprising an elastic member, wherein an end of the elastic member is connected to the case, and the other end of the elastic member is connected to the liquid guiding member; when the liquid guiding member is driven by an external force to move along the central axis of the case towards the needle outlet port, the elastic member is elastically deformed to drive the liquid guiding member to move back to an initial position of liquid guiding member.

19. A tattoo device, comprising an introduction needle and an external drive member, wherein,
the introduction needle comprises a needle piercing portion and a liquid guiding member, the needle piercing portion comprises a piercing projection, the piercing projection is disposed on an end of the liquid guiding member, the piercing projection includes a substrate and a needle tooth, the needle tooth is fixedly arranged on a side surface of a side of the substrate, a central axis of the needle tooth is perpendicular to the side surface of the substrate; the liquid guiding member is columnar; a side surface of the other side of the substrate is fixed to the end of the columnar liquid guiding member, a central axis of the columnar liquid guiding member is parallel to the central axis of the needle tooth; and
the external drive member is configured to drive the liquid guiding member of the introduction needle to move.

* * * * *